(12) United States Patent
Sun et al.

(10) Patent No.: US 6,231,875 B1
(45) Date of Patent: May 15, 2001

(54) ACIDIFIED COMPOSITION FOR TOPICAL TREATMENT OF NAIL AND SKIN CONDITIONS

(75) Inventors: Ying Sun, Somerville; Jue-Chen Liu, Neshanic; Elizabeth Kimbleton, Princeton; Jonas C. T. Wang, Robbinsville, all of NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 09/265,284

(22) Filed: Mar. 9, 1999

Related U.S. Application Data
(60) Provisional application No. 60/080,116, filed on Mar. 31, 1998.

(51) Int. Cl.$^7$ ............... A61K 7/00; A61K 7/04; A01N 25/34
(52) U.S. Cl. ............ 424/401; 424/61; 424/404
(58) Field of Search ............ 424/401, 61, 78.03, 424/404

(56) References Cited

U.S. PATENT DOCUMENTS

| | | | |
|---|---|---|---|
| 4,956,467 | 9/1990 | Hinman et al. | 548/112 |
| 4,957,730 | 9/1990 | Bohn et al. | 424/61 |
| 5,122,533 | 6/1992 | Bar-On et al. | 514/390 |
| 5,264,206 | 11/1993 | Bohn et al. | 424/61 |
| 5,461,068 * | 10/1995 | Thaler et al. | 514/399 |
| 5,683,713 | 11/1997 | Blank et al. | 424/449 |
| 5,696,164 | 12/1997 | Sun et al. | 514/562 |
| 5,958,458 * | 9/1999 | Norling et al. | 424/490 |

FOREIGN PATENT DOCUMENTS

| | | |
|---|---|---|
| 1 000 567 | 12/1953 | (DE) . |
| 0 440 298 A1 | 1/1991 | (EP) . |
| 0 499 882 A1 | 2/1992 | (EP) . |
| 2 689 008 | 3/1992 | (FR) . |
| 534 810 A1 | 8/1992 | (FR) . |
| WO 88/06884 | 9/1988 | (WO) . |
| WO 94/16991 | 8/1994 | (WO) . |
| WO 96/19186 | 6/1996 | (WO) . |
| WO 97/28790 | 8/1997 | (WO) . |

OTHER PUBLICATIONS

PCT International Search Report dated Jul. 6, 1999.
PCT Search Report dated Aug. 24, 2000.
PCT Search Report dated Sep. 24, 1999.
Walters, Kenneth A., "Penetration of Chemicals into, and through, the Nail Plate", Pharmacy International, Apr. 1985, pp. 86–89.
Kobayasi et al., "Enhancing Effect of N–Acetyl–L–Cysteine or 2–Mercaptoethanol on the In Vitro Permeation of 5–Fluorouracil or Tolnaftate Through the Human Nail Plate", Chem. Pharm. Bull, Nov. 1998, pp. 1797–1802.

* cited by examiner

Primary Examiner—Thurman K. Page
Assistant Examiner—S. Howard

(57) ABSTRACT

This invention relates to a method for topical treatment of human nail and skin diseases, including fungal infections, bacterial infections, and psoriatic infections. In addition, this invention relates to a method of treating the general condition of human nails including their strength, rate of growth and appearance. More particularly, the invention relates to an acidified composition and methods of using said composition. Still further the invention relates to an acidified lacquer useful in treating human nails and skin.

48 Claims, 7 Drawing Sheets

ACIDIFIED COMPOSITION FOR TOPICAL TREATMENT OF NAIL AND SKIN CONDITIONS

This application claims benefit of provisional application No. 60/080,116, filed Mar. 31, 1998.

FIELD OF THE INVENTION

This invention relates to a method for topical treatment of human nail and skin diseases, including fungal infections, bacterial infections, and psoriatic infections. In addition, this invention relates to a method of treating the general condition of human nails including their strength, rate of growth and appearance. More particularly, the invention relates to an acidified composition and methods of using said composition. Still further the invention relates to an acidified lacquer useful in treating human nails and skin.

BACKGROUND OF THE INVENTION

Onychomycosis is a fungal disease of the human nail. The symptoms of this disease are a split, thickened, hardened, and rough nail plates. This is caused by any of a number of organisms and is particularly prevalent in the elderly. Typically fungal infections are treated by topical application of antifungal agents and/or oral administration of antifunal agents. Unlike other fungal infections, there is no topical treatment for onchomycosis which is approved by the United States Food and Drug Administration. It is desirable to treat this disease topically due to the potential for side effects which have been associated with some of the oral treatment regimens. One reason for the absence of a topical treatment is that in this disease, the symptomatic thickened nail plate prevents topical agents from reaching the site of the infection. The target sites for the treatment of onychomycosis reside in the nail plate, nail bed and nail matrix, as set forth in FIG. 1. It has been shown that if the nail barrier is modified, reduced, or eliminated, topical antifungal drug treatment is effective for onychomycosis. For example, both miconazole and ketoconazole have been demonstrated to be effective in topically treating onychomycosis after nail removal. Nevertheless, most consumers would certainly prefer a less dramatic treatment of nail fungal infection than removal of the nail.

The nail plate is thick, hard, dense, and represents a formidable barrier for drugs to be able to penetrate in a therapeutically required quantity. Although nail material is similar to the stratum corneum of the skin, being derived from epidermis, it is composed primarily of hard keratin, which is highly disulfide-linked, and is approximately 100-fold thicker than stratum corneum. In order to deliver a sufficient amount of drug into the nail plate, the permeability of the nail plate to the drug must be enhanced. This is particularly true in fungal diseases where a common symptom of the disease is thickened nail plate. In an onychomycosis study, patients' small toe nails were 5 mm and their large toe nails were 9 mm. When compared to non-infected nail dimensions of 0.5 mm for small toe nails and 1.5 mm for big toe nails, the infected nail presents a formidable barrier to topical treatment.

Nail plates have a high sulphur content in the form of disulfide bonds. U.S. Pat. No. 5,696,164 (Sun et al., 1997) discloses the use of thio-containing amino acids and its derivatives (i.e., sulfhydryl-containing amino acids), such as cysteine and N-acetyl cysteine, and urea to increase drug permeability in a nail plate, by breaking disulfide bonds in nail keratin to increase drug penetration into and through the nail. It was shown that a significant enhancement in topical drug delivery through nail was achieved. European Patent Application EP 503988 A1 (1992) discloses a composition to treat onychomycosis, comprising nail-penetration agents, such as glycols, glycol ethers, dimethyl sulfoxide, caprolactam, and other hydrophilic compounds to facilitate the penetration of allylamine fungicides into the nail.

Nail lacquer, also known as nail coating, polish, enamel and/or varnish, is a popular form of nail care products. A drug-containing nail lacquer is the most convenient and most acceptable nail treatment method to treat nail diseases such as onychomycosis and psoriasis-affected nail. As described above, it is essential to have a drug-containing nail lacquer that is capable of delivering a drug or drugs into and through the nail in therapeutically sufficient quantity. In addition, the drug-containing lacquer should not be irritating to the skin tissue adjacent to the nail. The drug in the lacquer formulations should be stable enough to meet the normally required 2-year shelf life for a pharmaceutical product.

Nail lacquers containing therapeutic agents have been known in the past. For example, U.S. Pat. No. 4,957,730 (1990) describes a nail varnish containing a water-insoluble film-forming substance and antimycotic compound. U.S. Pat. No. 5,120,530 (1992) describes a antimycotic nail varnish containing amorolfine in quaternary ammonium acrylic copolymer. The water-insoluble film former is a copolymerizate of acrylic acid esters and methacrylic acid esters having a low content of quaternary ammonium groups. U.S. Pat. No. 5,264,206 (1993) describes a nail lacquer with antimycotic activity, which contains an antimycotic agent and water-insoluble film formers including polyvinyl acetate, a copolymer of polyvinyl acetate and acrylic acid, copolymers of vinyl acetate and crotonic acid, monoalkyl maleate, etc. U.S. Pat. No. 5,346,692 (1994) describes a nail lacquer for treating onychomycosis, comprised of a film-forming agent, an antimycotically active substance, and urea, wherewith the antimycotic agent and urea are liberated from the lacquer when the lacquer is applied. A preferred formulation comprises cellulose derivatives as film former, clotrimazole as the antimycotic agent, dibutyl phthalate as a plasticizer, and a mixture of acetone and ethanol as solvent. U.S. Pat. No. 5,487,776 (1996) describes a nail lacquer composition which forms a water permeable film containing griseofulvin when the organic solvent system evaporates, wherein a portion of the griseofulvin is in solution and a portion of griseofulvin is present as a colloidal suspension. European Patent Application EP515312 A2 (1992) describes a nail lacquer containing terbinafine or its hydrochloric acid salt as an antimycotic agent, solvents, and a polymeric film former consisting of di-butyl phthalate, Paraloid A-21 acrylic resin, poly(vinyl acetate) etc. However, these patents and publication mention little, if any, information concerning nail penetration enhancement of drugs in these disclosures.

Notwithstanding these instances, however, simply placing a drug in a conventional lacquer formulation without any means of enhancing nail penetration through the nail is unlikely to achieve the desired therapeutic goal. This is particularly true with certain classes of antifungal medication, particularly, azoles and imidazoles. These drugs are often quite insoluble and therefore it is difficult to prepare topical formulations of these drugs. Furthermore, many topical imidazole formulations have been known to be extremely irritating.

Furthermore, when treating onychomycosis, once the nail fungi are killed, the replacement non-infected nails grow relatively slowly. Thus, it can take from six months for non-infected finger nails, and 12 to 18 months for non-infected toe nails to grow and replace discolored and/or deformed. Preferably, a topical product for nail disease treatment, such as onychomycosis, is not only efficacious in eliminating the fungi, but in shortening the waiting period for the healthy nail to grow. U.S. Pat. No. 4,927,626 (1990) describes the topical application of minoxidil to increase the growth of unguis in animals, including human nail. However, it neither describes nor suggests how to deliver the minoxidil through the nail.

The recurrence rate of onychomycosis is relatively high for the patients who have been treated and considered "cured". Because certain people are more prone to onychomycosis, prophylactic products, such as a drug-containing lacquer, are desirable to prevent the relapse of onychomycosis.

Aside from the antifungal diseases associated with nails, there are antifungal diseases associated with human skin. One particular sight of infection is the feet where diseases associated with ring worm, commonly known as athlete's foot, are prevalent.

There are a number of commercial treatments for this disease containing miconazole nitrate as the active ingredient. However, despite these commercial products, a formulation which is capable of delivering a greater percentage of the active ingredient than the commercial products would be useful.

Therefore it is an object of the current invention to prepare a drug-containing composition which is capable of delivering a drug or drugs into and through human nails and skin in a therapeutically sufficient quantity. In addition it is an object of this invention to prepare a composition which adheres to the nail and skin for a prolonged period of time. Further it is an object of the invention to prepare a composition which is non-irritating to human skin. It is still further an object of the invention to prepare a lacquer containing said composition. Further, the composition containing lacquer should not be irritating to the skin tissue adjacent to the nail. Further still, the composition and lacquer should have the shelf required of a pharmaceutical product.

SUMMARY OF THE INVENTION

The present invention provides an acidified composition to treat nail and skin diseases such as onychomycosis, psoriatic nails, psoriasis of the skin, versicolor, ringworm, plantar tinea pedis, Jock itch, and athlete's foot.

Particularly, the invention includes an acidified composition comprising at least one active agent, at least one acidifier, and at least one volatile solvent. Further, the invention includes a method of treating disease infected human nails or skin by topically applying 1) an acidified composition comprising at least one acidifier, at least one volatile solvent, and at least one active agent; or 2) an acidified lacquer composition comprising at least one acidifier, at least one volatile solvent, at least one active agent, and at least one polymeric film former. Still further, the invention includes a method of improving and promoting healthy human nails and skin by topically applying 1) an acidified composition comprising at least one acidifier, at least one volatile solvent, and at least one active agent; or 2) an acidified lacquer composition comprising at least one acidifier, at least one volatile solvent, at least one active agent, and at least one polymeric film former.

In addition, the invention contemplates an acidified lacquer composition comprising at least one active agent, at least one acidifier, at least one volatile solvent, and at least one polymeric film former.

DETAILED DESCRIPTION OF THE INVENTION

Figure 1:
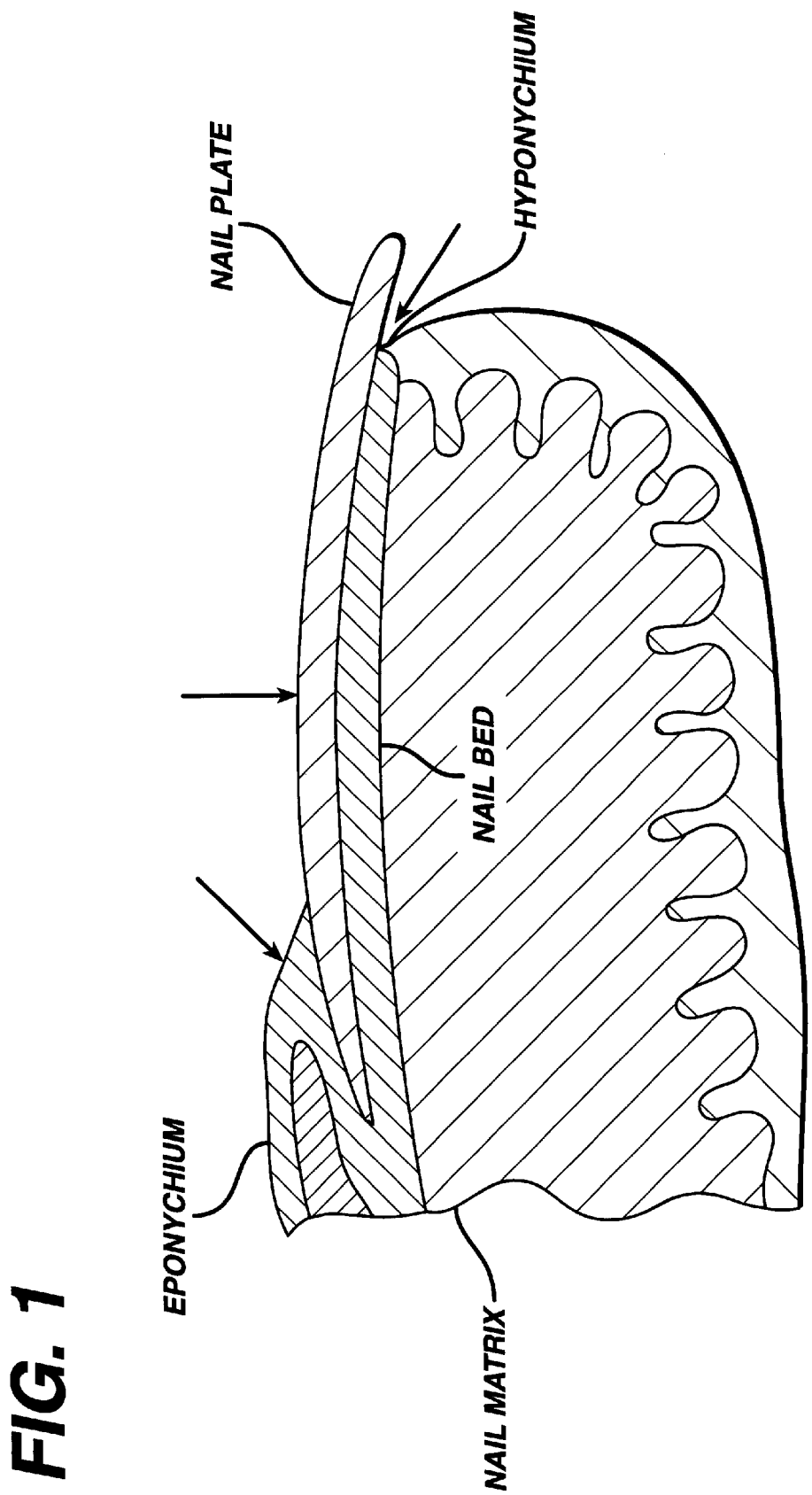
FIG. 1 is a depiction of the target sites for the treatment of onychomycosis.

This invention relates an acidified composition comprising at least one active agent, at least one acidifier, at least one volatile solvent, and at least one active agent.

As used herein the term "acidifier" refers to substances which are liquids having an apparent pH of $\leq 1$, or solids having a $pKa \leq 5$. Apparent pH is the pH reading measured by a glass pH electrode. The preferred acidifiers are 37% HCl, 10% HCl, sulfuric acid, o-phosphoric acid, nitric acid, acetic acid, L (+)-lactic acid, salicylic acid, and glycolic acid. The particularly preferred acidifiers are 37% HCl and 10% HCl. If the total weight of the acidified composition is 100 parts, the acidifier should be about 0.05 to about 50% w/w (w/w=weight/weight), preferably, from about 0.1% to about 10%, more preferably form about 0.5% to about 5%.

The term "volatile solvent" refers to liquid substances which evaporate more rapidly than water. The volatile solvent need not be anhydrous but should have less than 30%, preferably less than 10% with most preferably less than 2% water. Examples of such solvents include but are not limited to ethyl alcohol, isopropyl alcohol, ethyl acetate, butyl acetate, acetone, and mixtures thereof. The preferred volatile solvents are ethyl alcohol, isopropyl alcohol, ethyl acetate, and butyl acetate. If the total weight of the acidified composition is 100 parts, preferably, the volatile solvent is 90–98% w/w.

As used herein, the term "active agents" refers drugs for treating diseased nails, nutrients or nail conditioners which may be used to improve damaged nails or maintain healthy, and nail growth promoters which may be used on damaged or healthy nails. All of the aforementioned types of active agents may be used to treat the tissue surrounding the nail, and skin whether that tissue is healthy or diseased. The active agents include but are not limited to antifungal drugs used to treat onychomycosis and athlete's foot, antibiotics (or antiseptics) for bacterial infection of nails, tissue surrounding the nails and other human tissues, and antipsoriatic drugs for psoriatic nail and skin treatment. Examples of antifungal drugs include but are not limited to miconazole, econazole, ketoconazole, itraconazole, fluconazole, bifoconazole, terconazole, butoconazole, tioconazole, oxiconazole, sulconazole, saperconazole, clotrimazole, undecylenic acid, haloprogin, butenafine, tolnaftate, nystatin, ciclopirox olamine, terbinafine, amorolfine, naftifine, elubiol, griseofulvin, and their pharmaceutically acceptable salts. The preferred antifungal drugs are an azole, an allylamine, or a mixture thereof. Preferred azoles are selected from the group consisting of itraconazole, ketoconazole, miconazole, econazole, fluconazole, voriconazole, clotrimazole, butenafine, undecylenic acid, clioqinol, and their pharmaceutically acceptable salts. Preferred allylamines are selected from the group consisting of terbinafine, naftifine and mixtures thereof.

Examples of antibiotics (or antiseptics) include but are not limited to mupirocin, neomycin sulfate, bacitracin, polymyxin B, 1-ofloxacin, tetracyclines (chlortetracycline hydrochloride, oxytetracycline hydrochloride and tetrachycline hydrochoride), clindamycin phsphate, gentamicin sulfate, benzalkonium chloride, benzethonium chloride, hexylresorcinol, methylbenzethonium chloride, phenol, quaternary ammonium compounds, triclocarbon, triclosan, tea tree oil, and their pharmaceutically acceptable salts. Preferred antibiotics and antiseptics include mupirocin, neomycin sulfate, bacitracin, polymyxin B, 1-ofloxacin, tetracyclines, benzalkonium chloride, benzethonium chloride, triclocarbon, and triclosan.

Examples of antpsoriatic drugs include but are not limited to corticosteroids (e.g., betamethasone dipropionate, betamethasone valerate, clobetasol propionate, diflorasone diacetate, halobetasol propionate, amcinonide, desoximetasone, fluocinonide, fluocinolone acetonide, halcinonide, triamcinolone acetate, hydrocortisone, hydrocortisone verlerate, hydrocortisone butyrate, aclometasone dipropionte, flurandrenolide, mometasone furoate, methylprednisolone acetate), calcipotriene and anthraline. Preferred antipsoriatic drugs include betamethasone dipropionate, betamethasone valerate, and clobetasol propionate.

When the active agents are nail growth promoters, such agents include but are not limited to minoxidil, minoxidil sulfate, retinoids, cysteine and acetyl cysteine, methionine, glutathione, biotin, finasteride and ethocyn, as well as pharmaceutically acceptable salts of these compounds. The preferred growth promoter are minoxidil, minoxidil sulfate, retinoids, cysteine and acetyl cysteine. The particularly preferred nail growth promoters are 2% minoxidil, 2% minoxidil sulfate, and 0.1% retinol.

When the active agents include nutrients, they include but are not limited to vitamins, amino acids, and their derivatives. Examples of such agent include but are not limited to vitamin B complex: thiamine, nicotinic acid, biotin, pantothenic acid, choline riboflavin, vitamin $B_6$, vitamin $B_{12}$, pyridoxine, inositol, carnitine; ascorbic acid, ascorbyl palmitate, vitamin A, vitamin K, vitamin E, vitamin D, cysteine and N-acetyl cysteine, herbal extracts, and their derivatives.

When the active agents include nail conditioners they include but are not limited to mineral-containing compounds, flavonoids and retinoids. These nail conditioners improve general nail conditions, such as strengthening the nails to prevent nail chipping and cracking, and to beautify the nails. Examples of such agents include but are not limited to calcium pantothenate, calcium carbonate, and calcium gluconate. Examples of retinoids include but not limited to retinol (Vitamin A alcohol), retinal (Vitamin A aldehyde), retinyl acetate, etinyl palmitate, retinoic cid, 9-cis-retinoic acid and 13-cis-retinoic acid. When retinoids are the active agents, the concentration of retinoids is from about 0.01% to about 0.5%, preferably, from about 0.05 to about 0.1%. Examples of flavonoids include but not limited to naringenin, quercetin, catechins (e.g., epigallocatechin gallate), theaflavins, robustaflavone, hinokiflavone, amentoflavone, agathisflavone, volkensiflavone, morelloflavone, rhusflavanone, and succedangeaflavanone.

Overall, the preferred active agents are miconazole nitrate, itraconazole, econazole nitrate, ketoconzaole, clotrimazole, and terbinafine. If the total weight of the acidified composition is 100 parts, the active agent is present in about 0.05% to about 10% w/w, preferably, from about 0.1% to about 5%, more preferably from about 0.5% to about 2%.

Aside from the acidifier, the volatile solvent, and the active agent, the compositions of this invention may include other substances, such as preservatives, cosmetic additives, antioxidants, chelating agents and pigment flakes. Examples of such agents include but are not limited to benzoic acid, benzyl alcohol (as preservative), glycerol, propylene glycol as emollient, butylated hydroxyltoluene, butylated hydroxyanisole, ascorbic acid, ascorbyl palmitate, N-acetyl cysteine as antioxidant, citric acid, edetic acid and its sodium salts as chelating agent.

An example of a typical acidified composition comprises 1% clotrimazole as active agent, 0.1% concentrated HCl (37% HCl by weight) as acidifier, and 98.7% ethyl alcohol as volatile solvent. An example of a topical formulation containing this composition comprises 1% clotrimazole as active agent, 0.1% concentrated HCl (37% HCl by weight) as acidifier, 0.1% butylated hydroxyltoluene as antioxidant, 0.1% citric acid, and 98.7% ethyl alcohol as volatile solvent.

The invention includes an acidified lacquer composition comprising at least one active agent, at least one acidifier, at least one volatile solvent, and at least one polymeric film former. The terms, active agent, acidifier, and volatile solvent have their aforementioned meanings. The acidifier should be present at about 0.05 to 10% w/w, preferably, from about 0.1% to about 5%, more preferably form about 0.5% to about 2%. The volatile solvent should be present preferably, at about 70 to about 98% w/w. The active agent should be present at about 0.05% to 10% w/w, preferably, from about 0.1% to about 5%, more preferably from about 0.5% to about 2%.

As defined herein, the term "lacquer" refers to a liquid substance which typically dries to form a continuous or a non-continuous film by evaporation of the solvent.

As defined herein, the term "polymeric film former," is a polymer which may be added to a volatile solvent and other substances to form a polymeric solution which may be applied to the skin to form a film. Examples of polymeric film formers include but are not limited to acrylic copolymers/acrylic polymers, (such as Carboset® or Avalure® polymers, made by BF Goodrich); polymers of methacrylic acid and its esters (such as Eudragit® polymers: S, L, RS and RL series, made by Rohm Pharma); cellulose polymers, nitrocellulose, methyl cellulose, ethyl cellulose, cellulose acetates (such as cellulose triacetate, cellulose acetate butyrate); nylon, polyvinyl acetate, polyvinyl acetate phthalate, formaldehyde resin, and polymer blends of the aforementioned polymers. Preferred polymeric film formers are selected from the group consisting of acrylic copolymers/acrylic polymers, (such as Carboset® or Avalure® polymers, made by BF Goodrich); polymers of methacrylic acid and its esters, (such as Eudragit® polymers: S, L, RS and RL series, made by Rohm Pharma).

Lacquers may have different viscosities. The viscosity of the lacquer is related to the thickness of the film that will be left on a surface once the volatile solvent has evaporated. If one desires a thick and viscous lacquer, which will deposit a thick film on a surface, the concentration of the polymeric film former should be about 0.1% to about 30%, preferably from about 0.5% to about 15% of the total composition. If one desires a thin lacquer which will deposit a thin film on a surface, the concentration of the polymeric film former should be about 0.1% to about 15%, preferably about 0.5% to about 5.0% of the total composition.

The acidified lacquers of the invention may have other additives such as plasticizers (to maintain the pliability of the film formers), non-volatile drug solubilizers, cosmetic additives, and pharmaceutical additives.

When plasticizers and non-volatile drug solubilizers are used, examples of these substances include but are not limited to phthalate esters (e.g., dibutyl phthalate), citrate esters, triacetin, isopropyl myristate, N-methyl-2-pyrrolidone, fatty acids and fatty acid esters, propylene glycol, butylene glycol, hexylene glycol, propylene carbonate, poly-propylene glycol, methoxypolyethylene glycol, polyethylene glycol, glycerin. When plasticizers are used they are preferably about 0.001 to about 10% by weight of the total composition.

Pharmaceutical additives include but are not limited to antioxidants and chelating agents. Examples of antioxidants include but are not limited to butylated hydroxyltoluene, butylated hydroxyanisole, ascorbic acid, ascorbyl palmitate, N-acetyl cysteine. Examples of chelating agents include but are not limited to citric acid, edetic acid and its sodium salts. Cosmetic additives include, but are not limited to, coloring agents, fragrance, pigments, as well as powders of silica, zinc oxide, and titanium oxide.

A typical acidified lacquer composition comprises 1% clotrimazole as active agent, 0.1% concentrated HCl (37% HCl by weight) as acidifier, 15% acrylic polymer (Carboset® 525 or Avalure® AC 315) as film former, and 43% ethyl alcohol and 40% ethyl acetate as volatile solvents. The typical topical formulation containing the acidified lacquer composition comprises 1% clotrimazole as active agent, 0.1% concentrated HCl (37% HCl by weight) as acidifier, 15% acrylic polymer (Carboset® 525 or Avalure® AC 315) as film former, 0.7% isopropyl myristate as non-volatile drug solubilizer, 0.1% butylated hydroxyltoluene as antioxidant, 0.1% citric acid, and 43% ethyl alcohol and 40% ethyl acetate as volatile solvents.

A typical formulation containing the acidifed lacquer composition which may be used to treat onychomycosis, comprises from about 0.5 to about 3% of an antifungal drug as an active agent, from about 0.1% to about 1% concentrated HCl (37% HCl by weight) as an acidifier, about 15% acrylic polymer (Carboset® 525 or Avalure® AC 315) as a polymeric film former, 1% isopropyl myristate as non-volatile solvent, 0.1% butylated hydroxyltoluene as antioxidant, 0.1% citric acid, and 37% ethyl alcohol and 42.3%–42.7% ethyl acetate as volatile solvents.

A typical formulation containing the acidifed lacquer composition which may be used to treat vesicolor, psoriasis, ringworm, plantar tinea pedis, Jock itch, and athlete's foot comprises from about 0.5 to about 3% an antifungal drug as an active agent, from about 0.1% to about 1% concentrated HCl (37% HCl by weight) as an acidifier, 3% acrylic polymer (Carboset® 525 or Avalure® AC 315) as a polymeric film former, 1% isopropyl myristate as non-volatile solvent, 0.1% butylated hydroxyltoluene as antioxidant, 0.1% citric acid, and 67% ethyl alcohol and 24.3%–24.7% ethyl acetate as volatile solvents. The anti fungal drugs in the above examples can be selected from at least one of the following: clotrimazole, miconazole, terbinafine, amorolfine, ciclopirox olamine, tolnaftate, fluconazole, econazole, ketocoanzole, itraconazole, butenafine, and their pharmaceutically acceptable salts.

The invention includes a method of treating disease infected human nails or disease infected human skin by topically applying 1) an acidified composition comprising at least one acidifier, at least one volatile solvent, and at least one active agent; or 2) an acidified lacquer composition comprising at least one acidifier, at least one volatile solvent, at least one active agent, and at least one polymeric film former The terms, acidifier, volatile solvent, active agent, lacquer and polymeric film former were defined above.

The term "nail" means the horny cutaneous plate on the dorsal surface of the distal end of a finger or toe. FIG. 1 is a schematic diagram showing the basic anatomic structure of human nail and its surrounding tissues. The treatment contemplated by this invention is intended to deliver an active agent to the nail plate (the stratum corneum unguis) and to the nail bed (the modified area of epidermis beneath the nail, over which the nail plate slides as it grows) through the nail plate. Desirably, the active agent is also concurrently administered to the nail matrix (the proximal portion of the nail bed from which growth chiefly proceeds) and nail bed through the skin of the eponychium (commonly called the cuticle) and the hyponychium (the thickened epidermis underneath the free distal end of the nail).

The term "applying" refers to any method of physically transferring the acidified composition to the nail and the skin. Such methods include but are not limited to painting the composition or lacquer on the surface of the nail; spraying the composition or lacquer using a spray pump, and combining the composition or lacquer with a propellant so that it sprayed on the skin as an aerosol. The term "aerosol" refers to systems consisting of "pressurized packages" with either compressed gases or liquefied gases as propellants. Examples of compressed gases are compressed nitrogen and air. Examples of liquefied gas propellants are propane, isobutane, n-butane, dimethyl ether, and mixtures thereof. The preferred propellants are dimethyl ether, and mixture of dimethyl ether and one or more hydrocarbon propellants. The preferred weight ratio of dimethyl ether to the hydrocarbon propellant(s) ranges from greater than or equal to about 3:2 ($\geq 3.2$) respectively.

Typically for the treatment of nail diseases, the composition or lacquer is initially applied for once or twice per day and may be reduced to once or twice a week depending upon the intensity and resilience of the underlying infection.

As used herein the term "disease" refers to fungal diseases, bacterial diseases and psoriasis.

The fungal diseases of the human nail that can be treated in accordance with the invention include but are not limited to "onychomycosis." This disease is typically caused by an infection of *Epidermophyton floccosum*, several species of Trichophyton, such as *T. rubrum* and *T. mentagrophytes*, or yeast, such as *Candida albicans*, or molds. Fungal diseases of the human skin that can be treated in accordance with the invention include but are not limited to the diseased portions of the skin surrounding a nail especially to the eponychium, i.e., the skin tissue above the nail matrix. This application allows antifungal drug and nail growth promoters to be absorbed into the eponychium and subsequently into the nail matrix. This is particularly beneficial, for when the nail growth is accelerated, some antifungal drug is incorporated into the growing healthy nail to prevent re-infection by fungi. In addition to onychomycosis, fungal skin diseases such as versicolor, ringworm, psoriasis, athlete's foot, plantar tinea pedis, and Jock itch may be treated using the methods and compositions of this invention. Typically these skin diseases are caused by funguses such as *Trichophyton rubrum, T. mentagrophytes,* and *Epidermophyton floccosum.*

Typically the treatment regimen for skin fungal infections using the acidified composition or acidified lacquer can be once or twice per day, preferably once per day, with a duration from less than a week to four weeks, preferably equal or less than two weeks.

The topical treatment of the invention may be employed in combination with systemic treatment. For example, an antifungal drug, such as, itraconazole, terbinafine, griseofulvin or other antifungal drugs, can be given orally over a period of time. This time period may be concurrently during the entire topical treatment regimen, or concurrently during a portion (usually the latter phase) of the topical treatment regimen, or following the topical treatment.

The invention includes a method of treating healthy human nails or skin by topically applying 1) an acidified composition comprising at least one acidifier, at least one volatile solvent, and at least one active agent; or 2) an acidified lacquer composition comprising at least one acidifier, at least one volatile solvent, at least one active agent, and at least one polymeric film former Since the acidified composition and the acidified lacquer of the invention are non-irritating they may be used prophylactically to prevent infection. When used in this manner the acidified lacquer and acidified composition may be applied once or twice per month. Typically the prophylactic treatment regimen for fungal infections of the nail and skin using the acidified composition or acidified lacquer can vary from once or twice per week to once or twice per month, with the interval between treatments shorter for the skin and longer for the nail.

In order to illustrate the invention, the following examples are included. These examples do not limit the invention. They are meant to suggest a method of practicing the invention. Those knowledgeable in the treatment of human nails and skin may find other methods of practicing the invention. However, those methods are deemed to be within the scope of this invention.

EXAMPLES

As demonstrated in the following examples, various experiments were conducted in an effort to meet the requirement of a good topical therapeutic product: (1) enhanced drug delivery; (2) non-irritating to human issues involved; (3) good drug stability; and (4) convenient to use.

It has been demonstrated that antifungal drug uptake into human nails could be significantly increased by using the disclosed acidified lacquer compositions (Example 3, Table 4). In addition it has been demonstrated that even a greater drug uptake is found when the nails were pretreated with penetration enhancers (Example 5, Table 6), followed by use of the acidified lacquer compositions. It has also been demonstrated that skin substantivity of an antifungal drug against washing, as well as drug penetration into the skin, was drastically enhanced when the disclosed acidified lacquer composition was used in comparison to commercial products (Example 9, FIGS. 6 & 7).

Example 1

Acidification to Enhance Drug Uptake into Human Nail

To evaluate the effect of concentrated acids on miconazole nitrate solubility, 0.5% or 1.0% of the following acids was added into a liquid containing 2% miconazole nitrate and ethyl alcohol made up to 100%. The percentages are all by weight throughout the text. The tests were conducted at 22° C. under mixing.

As shown in Table 1, among many acids tested for the nail lacquer acidification, including concentrated hydrochloric acid, sulfuric acid, phosphoric acid, nitric acid, acetic acid, lactic acid, and glycolic acid, only concentrated HCl, and concentrated sulfuric acid to a less extent, could completely solubilize miconazole nitrate in ethyl alcohol. As used herein, complete solubilization means that the resulting mixture produces a clear solution. Furthermore, as can be seen in Table 1, this complete solubilization phenomenon only occurred with the concentrated hydrochloric acid, and to a less extent, with the concentrated sulfuric acid, but not with other acids tested.

TABLE 1

Miconazole Nitrate Solubility

| Concentrated Acid* | 0.5% acid added | 1.0% acid added |
|---|---|---|
| Hydrochloric acid | Clear solution | Clear solution |
| Sulfuric acid | Turbid suspension** | Turbid suspension** |
| o-phosphoric acid | Turbid suspension | Turbid suspension |
| Nitric acid | Turbid suspension | Turbid suspension |
| Acetic acid | Turbid suspension | Turbid suspension |
| L(+)-lactic acid | Turbid suspension | Turbid suspension |
| Glycolic Acid | Turbid suspension | Turbid suspension |

*Sources, grades, and pH measurements (with a glass electrode after 1 min) of the concentrated acids.

| acidifier | pH reading |
|---|---|
| Hydrochloric acid 37% USP/NF, Spectrum Chemical Mfg. Corp. | not available |
| Sulfuric acid, 95–98%, USP/NF Spectrum Chemical Mfg. Corp. | not available |
| o-phosphoric acid, 85% Certified ACS, Fisher Scientific. | not available |
| Nitric acid, 70.4% Reagent grade, Mallinckrdt. | not available |
| Acetic acid, 99.8% Glacial, J. t. Baker Chemical. | −0.19 to −0.28 |
| L(+)-lactic acid, 90% Fluka | 0.31 |
| Glycolic Acid, 70% Dupont | 0.43 |
| Salicylic acid, powder Spectrum Chem. | 2.92 |
| 0.1N HCl | 1.11 |
| 1.0N HCl | 0.21 |
| 10% HCl (w.v) | −0.18 |

**Turning into a clear solution when warming to 32° C.

Example 2

Drug Uptake into Human Nail Clippings from Acidified Solutions

To evaluate the effect of concentrated acids on miconazole nitrate uptake into human nail, an experiment was conducted as follows. One part of the acidifier (listed in Table 2) was added into a glass vial containing a liquid comprised of 2 parts of miconazole nitrate and 97 parts of ethyl alcohol (denatured, 200 proof). A known weight of human nail clippings was placed into the vial, which was then tightly capped. The nail partitioning experiment was conducted at 32° C. for 24 hours under mixing. At the end of the experiment, the nail clippings were thoroughly washed with alcohol to remove surface-bound drug. The miconazole nitrate content of the nail clippings was analyzed by High Pressure Liquid Chromatography (HPLC), and the results were tabulated in Table 2. It can be seen that the nail uptake of miconazole nitrate from the acidified solutions was enhanced by approximately 9 fold using 1% of hydrochloric acid or sulfuric acid; and 2–3 fold using the other acids tested.

TABLE 2

| Concentrated Acid (1%, w/w) | Miconazole nitrate uptake into nail clippings (mg drug/g nail) | Enhancement ratio Nail Conc.$_{with\ acid}$/Nail Conc.$_{without\ acid}$ |
|---|---|---|
| Hydrochloric acid | 1.39 | 9.27 |
| Sulfuric acid | 1.33 | 8.87 |
| o-phosphoric acid | 0.40 | 2.67 |
| Nitric acid | 0.48 | 3.20 |
| Acetic acid | 0.36 | 2.40 |
| L(+)-lactic acid | 0.48 | 3.20 |
| Glycolic Acid | 0.48 | 3.20 |
| Salicylic acid | 0.33 | 2.20 |
| Control: no acid added | 0.15 | — |

Example 3

Drug Uptake into Human Nail Clippings from Acidified Lacquer Formulations

Figure 2:
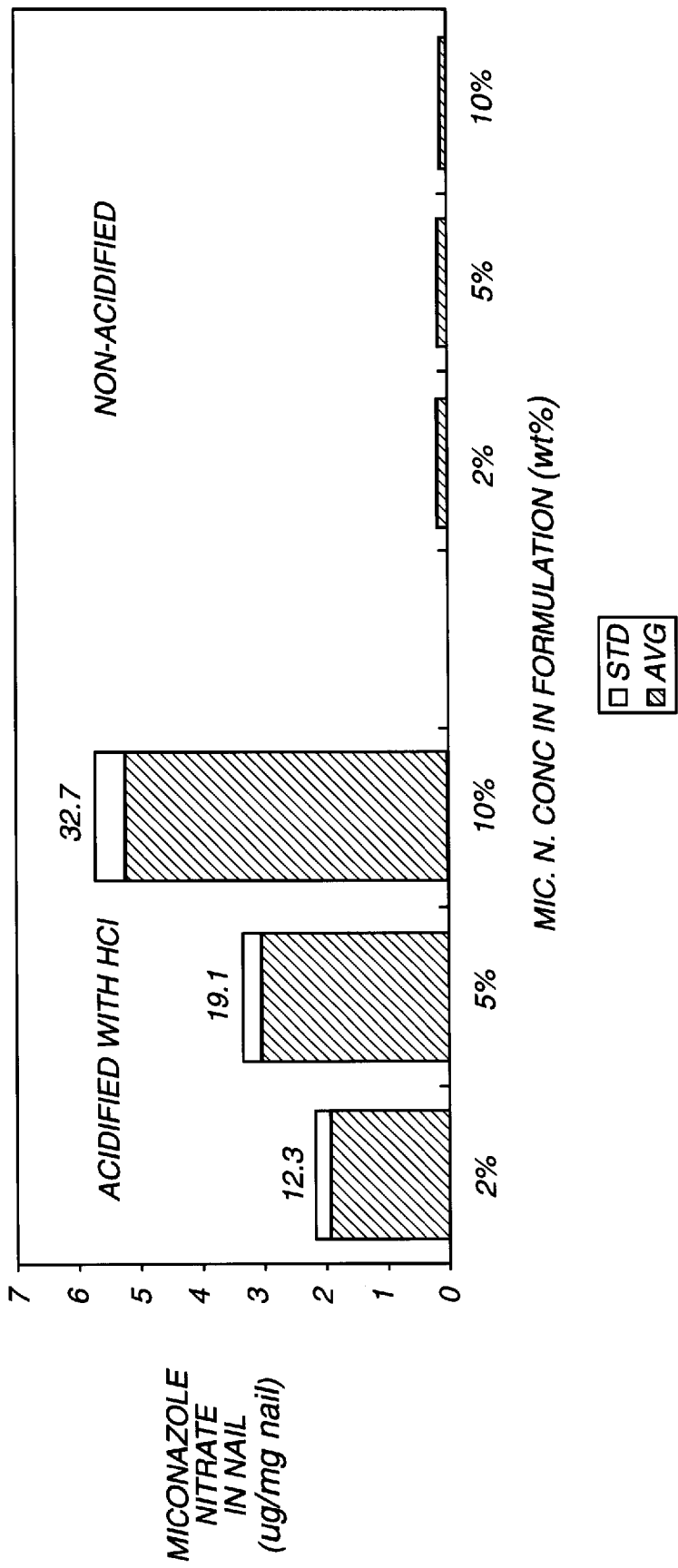
FIG. 2 is a graph of the drug partitioning results for miconazole nitrate lacquer formulations.
Figure 3:
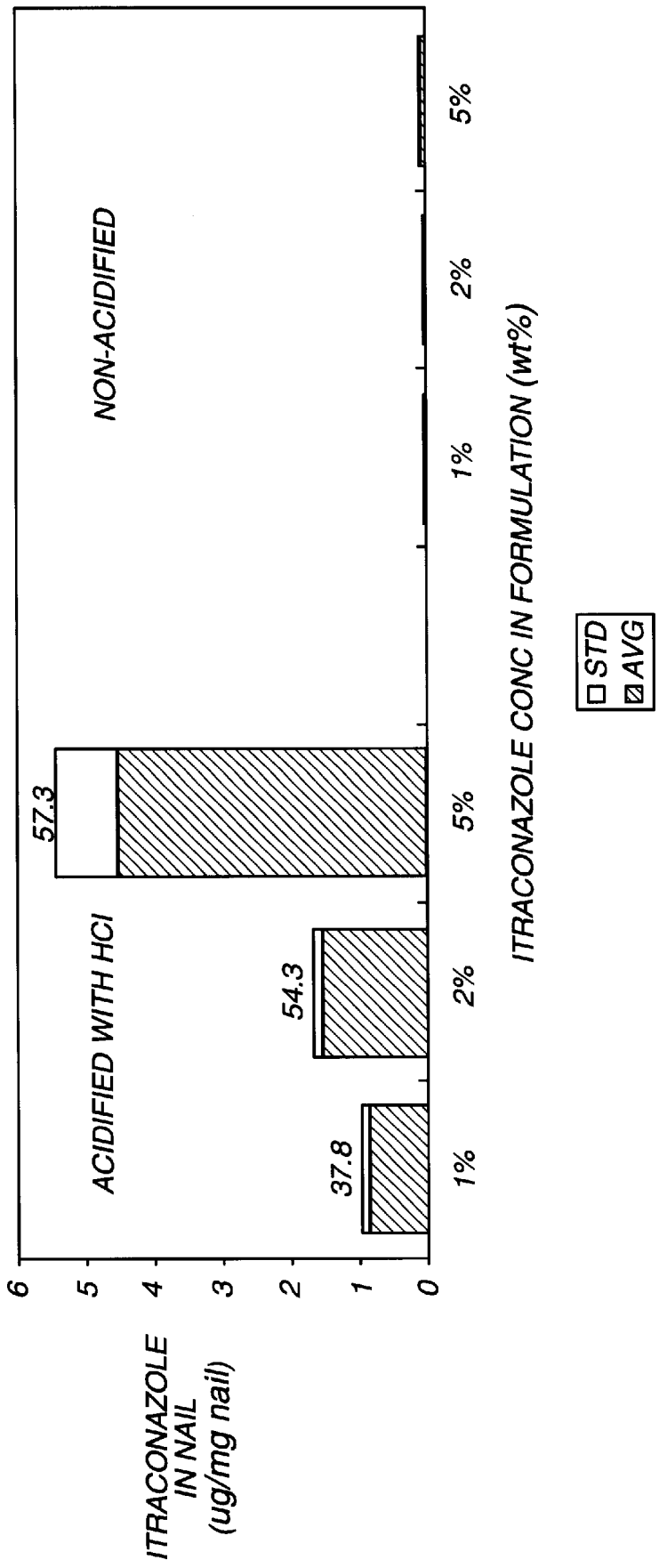
FIG. 3 is graph of the drug partitioning results for itraconazole lacquer formulations.

Drug partitioning studies were conducted to evaluate nail uptake of a drug by immersing human nail clippings in several lacquer formulations for 48 hours at 32° C. under constant stirring. At the end of the experiment, the drug content in the nail clippings was analyzed by HPLC after washing off the surface-bound drug. The nail lacquer formulations used in the drug partitioning studies are shown in the Table 3. The lacquer formulations contained either miconazole nitrate or itraconazole, with and without concentrate hydrochloric acid. The results of the drug partitioning into the nail shown in Table 4, FIG. 2 (miconazole nitrate) and FIG. 3 (itraconazole). The number on the bars in the figures are the enhancement ratio, which equals the nail drug content treated with a HCl-containing lacquer, divided by the nail drug content treated with a no-HCl-added-lacquer of the same drug concentration. As can be seen, an increase of 12–33 fold in drug uptake into nail was achieved with the miconazole nitrate lacquers; and a 38–57 fold increase with the itraconazole lacquers. These results clearly show that the acidified nail lacquer compositions significantly enhanced the penetration of antifungal drug miconazole nitrate and itraconazole into the nail.

TABLE 3

The compositions of lacquer formulations containing either miconazole nitrate or itraconazole used in the nail uptake experiments and Primary Dermal Irritation Test (in weight %)

| Formulation No. | Mic. N | Itra | Conc. HCl | IPM | Eth. Ac | EtOH | CBST 525 |
|---|---|---|---|---|---|---|---|
| 3-1 | 2.0 | 0 | 0.5 | 1.0 | 40.0 | 41.5 | 15.0 |
| 3-2 | 5.0 | 0 | 2.0 | 1.0 | 40.0 | 37.0 | 15.0 |
| 3-3 | 10.0 | 0 | 5.0 | 1.0 | 40.0 | 29 | 15.0 |
| 3-4 | 2.0 | 0 | 0 | 1.0 | 40.0 | 42.0 | 15.0 |
| 3-5 | 5.0 | 0 | 0 | 1.0 | 40.0 | 39.0 | 15.0 |
| 3-6 | 10.0 | 0 | 0 | 1.0 | 40.0 | 34.0 | 15.0 |
| 3-7 | 0 | 1.0 | 0.5 | 1.0 | 0 | 82.5 | 15.0 |
| 3-8 | 0 | 2.0 | 1.0 | 1.0 | 0 | 81.0 | 15.0 |
| 3-9 | 0 | 5.0 | 2.0 | 1.0 | 0 | 77.0 | 15.0 |
| 3-10 | 0 | 1.0 | 0 | 1.0 | 0 | 83.0 | 15.0 |
| 3-11 | 0 | 2.0 | 0 | 1.0 | 0 | 82.0 | 15.0 |
| 3-12 | 0 | 5.0 | 0 | 1.0 | 0 | 79.0 | 15.0 |

| | |
|---|---|
| Mic. N | Miconazole Nitrate |
| Itra | Itraconazole |
| Conc. HCl | Concentrate Hydrochloric Acid, 37% |
| IPM | Isopropyl Myristate |
| EtOH | Ethyl alcohol, 200 proof, denatured |
| CBST525 | Carboset ® 525, Acrylic copolymer, B F Goodrich |
| Eth. Ac | Ethyl Acetate |

Acidified lacquer formulations demonstrated enhanced drug uptake into human nail clippings. The nail uptake (nail partitioning) experiments were conduction in triplicates (n=3). The drug concentrations in the nail were the average value (AVG) with corresponding standard deviation (STD). The enhancement ratio of nail uptake of a drug was calculated by dividing the nail drug content treated with the acidified lacquer formulation of a particular drug concentration, over the nail drug content treated with a non-acidified lacquer containing the same drug concentration.

TABLE 4

| Formulation No. | Drug Conc. in lacquer formulation | A = acidified N = Non-acidified | Drug Content in nail (mg drug/ gm nail) AVG ± STD | Enhancement ratio of nail uptake: Content$_A$/ Content$_N$ |
|---|---|---|---|---|
| 3-1 | 1% Mic. N. | A | 1.888 ± 0.235 | 12.3 |
| 3-2 | 5% Mic. N. | A | 2.996 ± 0.314 | 19.1 |
| 3-3 | 10% Mic. N. | A | 5.255 ± 0.465 | 32.7 |
| 3-4 | 1% Mic. N. | N | 0.179 ± 0.033 | — |
| 3-5 | 5% Mic. N. | N | 0.157 ± 0.037 | — |
| 3-6 | 10% Mic. N. | N | 0.161 ± 0.016 | — |
| 3-7 | 1% Itra | A | 0.8212 ± 0.1253 | 37.8 |
| 3-8 | 2% Itra | A | 1.5089 ± 0.1263 | 54.3 |
| 3-9 | 5% Itra | A | 4.5497 ± 0.9011 | 57.3 |
| 3-10 | 1% Itra | N | 0.0217 ± 0.0107 | — |
| 3-11 | 2% Itra | N | 0.0278 ± 0.0159 | — |
| 3-12 | 5% Itra | N | 0.0794 ± 0.0314 | — |

Example 4

Skin Irritation Test

Despite the extremely strong acidity of the lacquer formulations, to our surprise, the nail varnish formulations are not irritating to the skin. A standard test for skin irritation, called "the Modified Draize Rabbit Primary Dermal Irritation Test" (PDI), was used to evaluate the acidified nail lacquers. The test procedures are described briefly as follows. The test skin sites of the New Zealand White albino rabbits were clipped free of fur. Skin abrasion was made at each test skin site using the barbed tip of a sterile 20 gauge hypodermic needle in a "tic-tac-toe" pattern. The nail lacquer was applied to the prepared test skin site. Observation was made by a skilled scientist in twenty four hours, and again in seventy two hours, for any signs of skin irritation, including erythema, eschar, and edema formation. A score system was used to grade the observed skin irritation:

ranging from the lowest score, 0 (non-rirritant) to the highest score 8 (severe irritant). The acidified lacquer formulations tested for PDI include Nos. 3-2, 3-3 and 3-9 (Table 3). All the acidified lacquers obtained the PDI score "mild". Another skin irritation test, called "Cumulative Skin Irritation Test" (CSI), was also conducted using the New Zealand White albino rabbits. The acidified nail lacquers were applied to the intact skin previously clipped free of fur (i.e., without previous skin abrasion) twice a week for two and one-half weeks. Prior to each lacquer application, the dried nail lacquer was first removed from the test skin using an alcohol swab containing 70% isopropyl alcohol.

Again, all the test results were mild (Table 5). The irritation potential of the acidified lacquer formulation was also evaluated on human volunteers. The nail lacquer was applied to the ventral forearm skin of three volunteers for twenty-four hours. There was no sign of any skin irritation. In one volunteer, once-a-day application of the lacquer was continued for two weeks. Prior to each lacquer application, the dried nail lacquer was first removed from the test skin using an alcohol swab containing 70% isopropyl alcohol. Again, no sign of skin irritation was observed.

It should be noted that the acidity of the nail lacquers was extremely high. Because of the anhydrous nature of the nail lacquers, any direct pH measurement did not have its normal meaning. However, to put the matter in perspective, consider the fact that the pH value of 0.1 N HCl is pH 1.0, whereas the content of the HCl in the nail lacquers tested in this study were up to five times higher than 0.1 N HCl. That a topical formulation containing such a high content of a strong acid is still mild to the skin, is truly surprising and completely unexpected.

application of an active-agent-containing formulation. The active agent may be of therapeutic or cosmetic value. Optionally, the pretreatment formulation containing enhancer(s) is also comprised of active-agents for therapeutic and cosmetic purposes. To demonstrate this methodology, experiments were conducted as follows. Human nail clippings of known weight were immersed in a pretreatment formulation containing NAC, urea and distilled water of certain concentrations at 32° C. under mixing for a period of time (e.g., 24 hours). At the end of the pretreatment procedure, the extent of nail swelling was determined by weighing the nail clippings after being blot-dried with paper towel. A drug uptake experiment was then carried out by immersion of the pretreated nail clippings in the acidified antifungal lacquer formulations at 32° C. under constant mixing for 48 hours. The basic composition of the acidified itraconazole lacquer formulations, and the nail uptake of drug procedures (i.e., nail partitioning) were the same as described in the previous sections. Table 6 tabulates the results of nail swelling after the pretreatment, and itraconazole uptake into the pretreated nail clippings. In general, the drug uptake increased as a result of pretreatment with nail penetration enhancers. The rank order of the enhancement with different pretreatment conditions are the following: urea alone<NAC alone<NAC plus urea. Pretreatment with urea alone showed rather limited enhancing effect on the drug uptake, whereas NAC alone was more effective. A combination of NAC and urea, on the other hand, showed a definite synergistic effect in the enhancement of drug uptake. For example, pretreatment with 20% urea alone resulted in 4.7 mg drug per gram nail; pretreatment with 10% NAC alone resulted in 15.45 mg drug per gram nail. In a sharp contrast, pretreatment with 10% NAC and 20% urea resulted

TABLE 5

The compositions of lacquer formulations containing either miconazole nitrate or itraconazole used in the Cumulative Skin Irritation Test (in weight %), and the test results

| Formula No. | Mic. N | Itra | Conc. HCl | IPM | Ascor. P | Eth. Ac | EtOH | CBST 525 | CSI |
|---|---|---|---|---|---|---|---|---|---|
| 4-1 | 5.0 | 0 | 2.5 | 1.0 | 0.1 | 40.0 | 36.4 | 15.0 | Mild |
| 4-2 | 0 | 5.0 | 2.5 | 1.0 | 0.1 | 0 | 76.4 | 15.0 | Mild |
| 4-3 | 2.0 | 0 | 1.0 | 1.0 | 0.1 | 40.0 | 55.4 | 0.5 | Mild |
| 4-4 | 0 | 0 | 2.5 | 1.0 | 0.1 | 40.0 | 41.4 | 15.0 | Mild |

| | |
|---|---|
| Mic. N | Miconazole Nitrate |
| Itra | Itraconazole |
| Conc. HCl | Concentrate Hydrochloric Acid, 37% |
| IPM | Isopropyl Myristate |
| Ascor. P | Ascorbyl Palmitate |
| Eth. Ac | Ethyl Acetate |
| EtOH | Ethyl alcohol, 200 proof, denatured |
| CBST | Carboset ® 525, Acrylic copolymer |

Example 5

Drug Uptake into Nail Clippings Which have been Pretreated with Penetration Enhancers Nail penetration enhancers such as N-acetyl cysteine (NAC) have been shown to promote drug penetration through human nail when a drug formulation contained the penetration enhancer and the drug (see U.S. Pat. No. 5,696,164). The invention describes a new enhancement method using NAC for topical drug delivery to the nail.

The essence of the new enhancing method is a nail pretreatment of nail penetration enhancer(s) prior to the in 28.46 mg drug per gram nail. The synergistic enhancement of two enhancers for drug uptake into the nail has an important and practical implication: it enable the use of a minimal amount of an enhancer which may be irritating to the skin at high concentration, such as NAC.

It should be noted that, in Table 6, the enhancement ratio of drug uptake into the nail is meant to compare the effect of pretreatment only. The acidified drug-containing lacquers were used in all the experiments, and the non-pretreated nail uptake data was used as the bench mark. On the other hand, a comparison can also be made between a non-acidified lacquer of certain drug concentration in a non-pretreated nail uptake experiment (as shown in Table 4) and an acidified lacquer of the same drug concentration in a pretreated experiment (as shown in Table 6). Thus another set of enhancement ratio data can be calculated: for itraconazole lacquer of 1%, there is a 463-fold increase in drug uptake into nail; for 2% itraconazole lacquer, there is a 826-fold increase; and for 5% itraconazole lacquer, there is a 759-fold increase, when the nail has been pretreated with 10% NAC and 10% Urea. This shows that the enhancing power of the combination (i.e., acidified lacquer and pretreatment) for drug delivery into nail are remarkable.

TABLE 6

Drug uptake into human nail from acidified itraconazole lacquer after pretreatment with nail penetration enhancers. All the experiments were conducted in triplicates (n = 3)

| DURING PRETREATMENT ($WT_{24\ hr}/WT_{Initial}$) × 100% Nail clippings immersed in pretreatment NAIL SWELLING solutions at 32° C. for 24 hours | | ITRACONAZOLE UPTAKE INTO NAIL (mg drug/gm nail) Followed by immersion in acidified lacquer formulations 32° C. for 48 hours | | | |
|---|---|---|---|---|---|
| AVG | STD | | AVG | STD | ENHANC. RATIO* |
| NO PRETREATMENT | | 1% ITRA | 0.82 | 0.12 | 1 |
| | | 2% ITRA | 1.51 | 0.13 | 1 |
| | | 5% ITRA | 4.55 | 0.9 | 1 |
| UREA ALONE | | | | | |
| 10% UREA | 1.31 | 0.18 | 2% ITRA | 4.71 | 0.85 | 3.1 |
| 20% UREA | 1.49 | 0.05 | 2% ITRA | 4.7 | 1.99 | 3.1 |
| NAC ALONE | | | | | |
| 10% NAC | 1.91 | 0.08 | 2% ITRA | 15.45 | 2.19 | 10.2 |
| 20% NAC | 2.73 | 0.34 | 2% ITRA | 30.86 | 3.48 | 20.4 |
| NAC + UREA | | | | | |
| 1% NAC + 10% UREA | 1.63 | 0.10 | 2% ITRA | 7.21 | 0.97 | 4.8 |
| 2% NAC + 10% UREA | 1.53 | 0.25 | 2% ITRA | 9.6 | 0.88 | 6.4 |
| 5% NAC + 10% UREA | 2.04 | 0.02 | 2% ITRA | 13.87 | 0.94 | 9.2 |
| 1% NAC + 20% UREA | 1.76 | 0.12 | 2% ITRA | 8.63 | 1.32 | 5.7 |
| 2% NAC + 20% UREA | 1.60 | 0.20 | 2% ITRA | 10.6 | 3.32 | 7.0 |
| 5% NAC + 20% UREA | 2.55 | 0.11 | 2% ITRA | 19.02 | 1.25 | 12.6 |
| 10% NAC | 1.91 | 0.08 | 2% ITRA | 15.45 | 2.19 | 10.2 |
| 10% NAC + 10% UREA | 2.66 | 0.10 | 2% ITRA | 24.83 | 1.67 | 16.4 |
| 10% NAC + 20% UREA | 3.52 | 0.21 | 2% ITRA | 28.46 | 4.37 | 18.8 |
| 20% NAC | 2.73 | 0.34 | 2% ITRA | 30.86 | 3.48 | 20.4 |
| 20% NAC + 5% UREA | 3.12 | 0.33 | 2% ITRA | 29.27 | 3.1 | 19.4 |
| 20% NAC + 10% UREA | 3.69 | 0.13 | 2% ITRA | 37.09 | 1.68 | 24.6 |
| 20% NAC + 20% UREA | 3.94 | 0.24 | 2% ITRA | 29.04 | 0.92 | 19.2 |
| ITRA CONC | | | | | |
| 10% NAC + 10% UREA | 2.50 | 0.10 | 1% ITRA | 10.05 | 0.67 | 12.3 |
| 10% NAC + 10% UREA | 2.50 | 0.10 | 2% ITRA | 22.97 | 1.74 | 15.2 |
| 10% NAC + 10% UREA | 2.50 | 0.10 | 5% ITRA | 60.24 | 5.99 | 13.2 |

*Enhancement ratio is defined as: the drug content in the pretreated nail divided by the drug content in the non-pretreated nail after immersion in a nail lacquer of the same drug concentration.

Example 6

Drug Permeation into and through Human Nail Plate

Experiments were conducted to evaluate the drug penetration through human nails. The experimental procedures are briefly described as follows: (1) human nail plates were mounted in modified Franz diffusion cells. (2) A nail enhancer formulation containing 10% NAC and 20% urea was placed in the donor cells to pretreat the nail plate for 24 hours. (3) After the pretreatment formulations were removed from the donor cells, lacquer formulations containing 2% or 5% miconazole nitrate were applied to the nail plate in the donor cells. At the end of one week from the starting of the nail pretreatment, the nail lacquers were removed with ethanol swabs. Steps (2) & (3) were repeated for three more weeks. The experiment was conducted in triplicate for a total length of four weeks at 32° C. (AVG±STD, n=3). The effect of occlusive versus non-occlusive conditions was tested by covering selected donor cells with an occlusive polymer film after allowing the lacquer sufficient time to dry up. The occlusion test was used to mimic the condition often caused by the "over-coat" layers of another nail lacquer. The amount of drug permeated through the nail plate was determined by analyzing the receptor fluid with HPLC. The drug concentration in the nail plate was determined.

Figure 4:
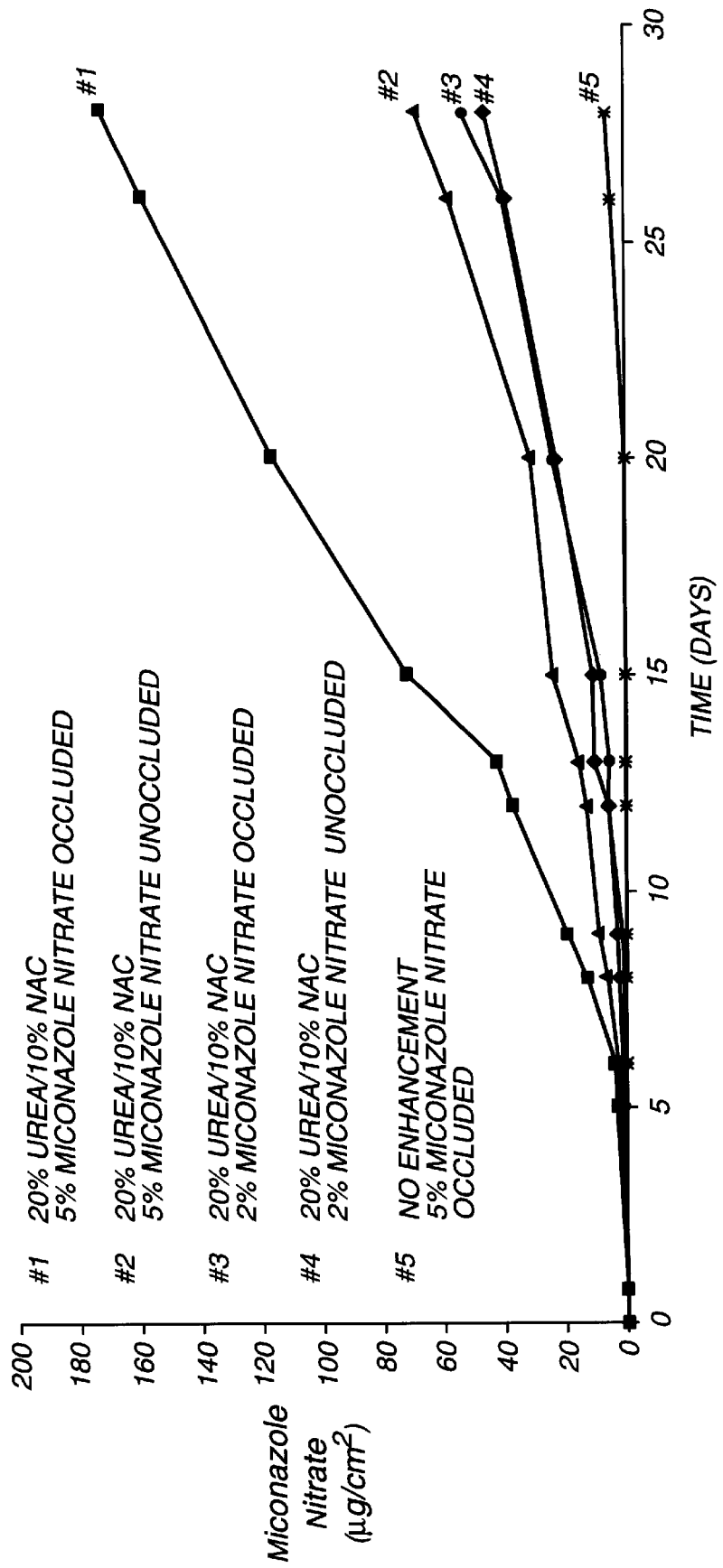
FIG. 4 is a graph of the permeation profiles for miconazole nitrate.

The nail permeation results were tabulated in Table 7 and plotted in FIG. 4. The permeation profiles in FIG. 4 shows that miconazole nitrate from the nail lacquers permeated through the nail plate rather rapidly, especially for those nail plates which had been pretreated with nail penetration enhancers (i.e., comparing #1–4 with #5). As can be seen from FIG. 5 and Table 7, the acidified nail lacquers delivered miconazole nitrate into and through the nail plates even without the help of nail penetration enhancers. Pretreatment with NAC and urea significantly increased the drug permeation through the nail. The lacquer containing a higher drug concentration delivered more drug through the nail. Occlusive condition further enhanced the drug permeation from the drug-containing lacquer. Occlusive conditions can be achieved easily by multiple coats of the drug-containing lacquer, or by "overcoats" of another lacquer, or by application of an occlusive cover, such as an adhesive-coated polymeric bandage of predetermined properties, such as certain range of moisture and gas permeabilities.

TABLE 7

Drug Penetration into and through human nail plate

| Permeation Conditions | Drug Permeated into receptor (cum µg/cm$^2$) | Drug in NAIL (µg/cm$^2$) | Total Amount Delivered (µg/cm$^2$) | Nail Thickness |
|---|---|---|---|---|
| Enhancer: 10% NAC & 20% urea 2% Mic. Nit. lacquer* | Unoccluded 45.92 ± 17.32 | 596.2 ± 82.3 (8856.4 µg/cm$^3$) | 642.10 | 0.0567 cm. |
| Enhancer: 10% NAC & 20% urea 2% Mic. Nit. lacquer* | Occluded 52.95 ± 7.54 | 814.0 ± 118.2 (12269 µg/cm$^3$) | 866.99 | 0.0596 cm |
| Enhancer: 10% NAC & 20% urea 5% Mic. Nit. lacquer (4-1) | Unoccluded 69.92 ± 60.05 | 1004.2 ± 100.9 (17365 µg/cm$^3$) | 1074.13 | 0.0542 cm |

TABLE 7-continued

Drug Penetration into and through human nail plate

| Permeation Conditions | Drug Permeated into receptor (cum µg/cm²) | Drug in NAIL (µg/cm²) | Total Amount Delivered (µg/cm²) | Nail Thickness |
|---|---|---|---|---|
| Enhancer: 10% NAC & 20% urea 5% Mic. Nit. lacquer (4-1) | Occluded 172.94 ± 71.74 | 1264.8 ± 520.6 (18586 µg/cm³) | 1437.7 | 0.0559 cm |
| No enhancer: 5% Mic. Nit. lacquer (4-1) | Occluded 6.04 ± 5.59 | 242.1 ± 98.9 (6007 µg/cm³) | 248.11 | 0.0339 cm |

*Similar composition to 4-1, but with a lower drug concentration.

Example 7

Skin Permeation Experiment

Figure 5:
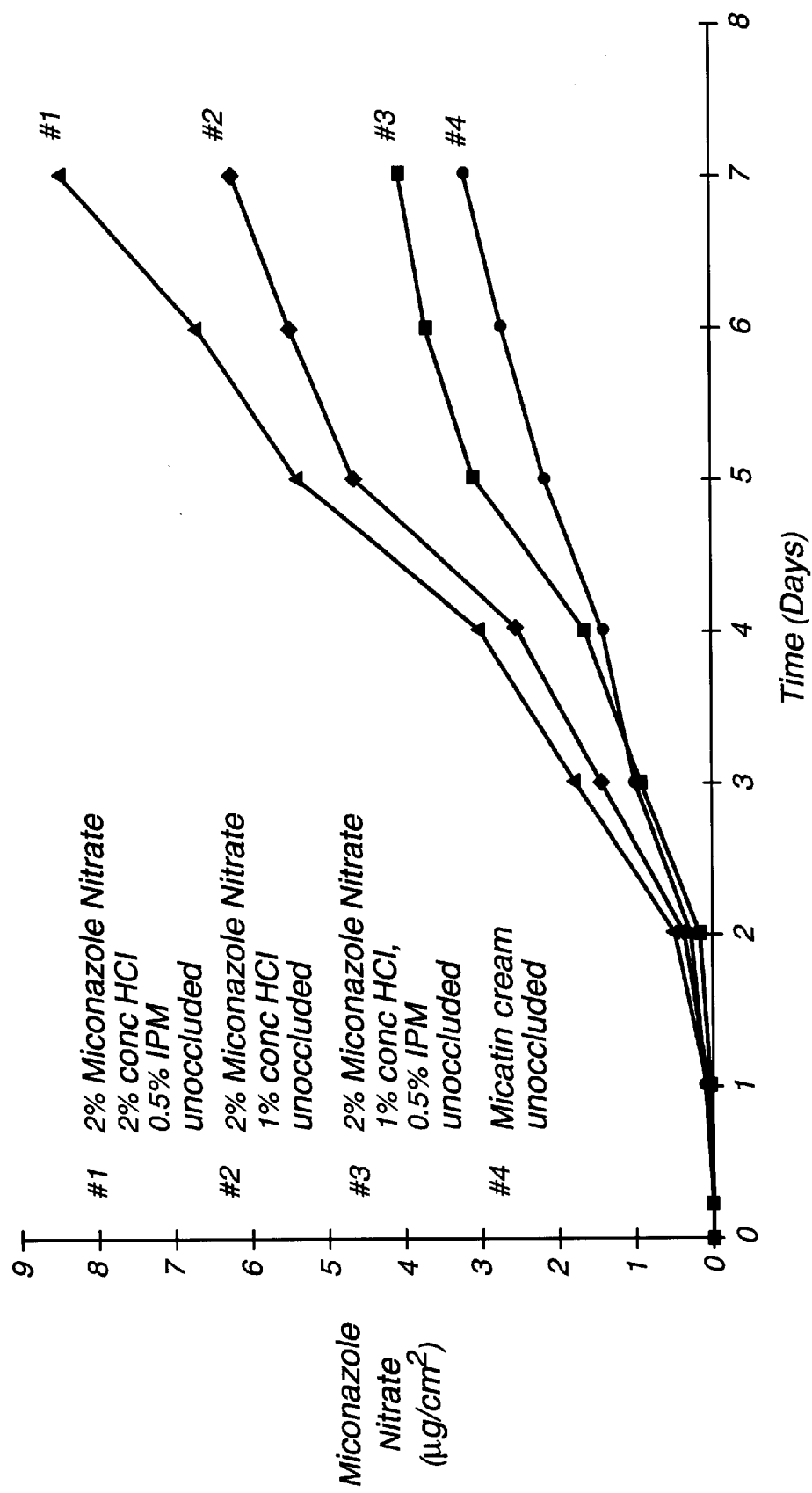
FIG. 5 is a graph of the permeation of miconazole nitrate lacquers.

To evaluate whether the drug-containing lacquer formulation can be used to deliver drug into the skin, a skin permeation study was conducted by applying a lacquer formulation containing 2% miconazole nitrate to a solvent evaporated in a short period of time, and left a uniform polymer film on the skin. Table 8 tabulates the compositions of the nail lacquer formulations tested. A commercial cream product containing 2% miconazole nitrate (Micatin Cream) was also tested for comparison purpose. The amount of miconazole nitrate penetrated through the skin and reached the receptor was analyzed by HPLC. The skin content of the drug, i.e., that retained in the dermis, was also determined by HPLC. Results in Table 9 and FIG. 5 show that miconazole nitrate was indeed able to diffuse out of the lacquer layer and to penetrate through the human skin. All the miconazole nitrate-containing lacquers delivered more drug into the skin. A comparison of Formulation Nos. 7-3 with 7-4 show that a higher HCl content in the lacquer led to a higher skin permeation of the drug, indicating the acid acted like a penetration enhancer in this situation.

Depending on the polymer content, the acidified formulations can be formulated as lacquer or spray and aerosol. A lacquer formulation contains relative high polymer content, and forms a polymer film upon application. On the other hand, a low-polymer-content formulation can be sprayed by a pump operated manually, or powered by compressed or liquefied gases, i.e., in the forms of liquid spray or aerosol. In fact, one of the formulations (i.e., No. 4-3) in Table 5 tested for skin irritation was formulated specifically as liquid spray. It contained only 0.5% Carboset® 525 as polymer film former, instead of 15% polymer in the other lacquers. After being applied to skin with a spray pump, this formulation formed an almost invisible, discrete layer on the test skin site.

TABLE 8

The compositions of lacquer formulations containing miconazole nitrate used in the skin permeation study (in weight %)

| Formula No. | Mic. N. | Conc. HCl | IPM | EtOH | CBST 525 |
|---|---|---|---|---|---|
| 7-1 | 2 | 1 | 0 | 87.0 | 10 |
| 7-2 | 2 | 2 | 0 | 86.0 | 10 |

TABLE 8-continued

The compositions of lacquer formulations containing miconazole nitrate used in the skin permeation study (in weight %)

| Formula No. | Mic. N. | Conc. HCl | IPM | EtOH | CBST 525 |
|---|---|---|---|---|---|
| 7-3 | 2 | 1 | 0.5 | 86.5 | 10 |
| 7-4 | 2 | 2 | 0.5 | 85.5 | 10 |

Control (Bench mark): Micatin Cream containing 2% miconazole nitrate in a cream base.

TABLE 9

Results of miconazole nitrate skin permeation from acidified lacquer formulations (AVG ± STD, n = 3)

| Formulation | Average Amount Permeated (cum µg/cm²)/7 days | Average Amount in Dermis (µg/cm²) |
|---|---|---|
| 7-1 2% Mic. N., 1% conc HCl | 5.99 ± 0.68 | 10.13 ± 0.31 |
| 7-3 2% Mic. N., 1% conc HCl, 0.5% IPM | 3.84 ± 1.38 | 12.88 ± 3.61 |
| 7-4 2% Mic. N., 2% conc HCL, 0.5% IPM | 8.24 ± 1.82 | 13.52 ± 3.63 |
| Micatin Cream | 2.96 ± 1.60 | 9.44 ± 4.44 |

Example 8

Drug Stability in Acidified Lacquer

To evaluate the drug stability in the acidified lacquer formulations, accelerated drug stability tests were conducted at elevated temperatures over certain periods of time (a method widely applied in pharmaceutical industry). The stability results for the formulations tested (e.g., Formulations 4-1, 4-3, 3-8, and 3-9) indicate that the drug formulations are stable in the acidified lacquers, and would satisfy the required two-year shelf life. This is a surprise since it is well known that the presence of a strong acid usually cause drug decomposition through acid-induced degradation reactions.

Example 9

Increased Skin Substantivity of Miconazole Nitrate by the Present Invention

The purpose of this experiment was to examine the skin substantivity of the antifungal drug miconazole nitrate from a liquid spray formulation as an example of the present invention. This liquid spray (hereto, the Spray Formulation) was compared to two commercial products for athlete's foot treatment, which contained the same drug and concentration as the Spray Formulation. In the U.S., topical antifungal products containing 2% miconazole nitrate for athlete's foot treatment require a regimen of twice-a-day application and duration of four weeks. If skin substantivity of miconazole nitrate can be improved (i.e., drug retention on the skin is increased), a more patient-friendly product can be made with a far less frequent dosing regimen and a much shorter therapy duration.

In vitro skin permeation tests combined with a washing procedure were conducted using dermatomed human cadaver skin mounted on Franz diffusion cells (n=6). The three formulations tested were the Spray Formulation, Micatin® cream (hereinafter Formula A) and Lotrimin® spray liquid aerosol (hereinafter Formula B). Table 10 shows all the compositions of the preparations tested.

TABLE 10

Compositions of the preparations tested

Formula A:

Miconazole nitrate (2%) — active ingredient
Benzoic acid
BHA
Mineral Oil
Peglicol 5 Oleate
Pegoxol 7 Stearate
Purified water Formula B:

Miconazole Nitrate (to deliver 2%) — active ingredient
Alcohol SD-40 (17% w/w)
Cocamide DEA
Isobutane
Propylene glycol
Tocopherol (Vitamin E)

The Spray Formulation

| Ingredient | % (w/w) |
| --- | --- |
| Miconazole Nitrate, USP | 2.00 |
| Isopropyl Myristate, USP | 1.00 |
| Ethyl Alcohol (40B), USP | 70.00 |
| Avalure Polymer | 3.00 |
| Menthol, USP | 1.00 |
| Ethyl Acetate, USP | 22.00 |
| Conc. HCl, USP | 1.00 |

To begin the experiment, a test formulation was applied to the skin surface to form a thin layer. At 0.5, 12, or 24 hours, a washing procedure was conducted to mimic normal shower/bath by washing the skin surface with 5 milliliters of warm water (32° C.). At the end of the 24-hour permeation test, miconazole nitrate retained on the skin surface was removed with methanol swabs, and the epidermis was separated from dermis. The drug content in wash liquids, methanol swabs, epidermis, dermis, and receptor media was analyzed by HPLC.

Figure 6:
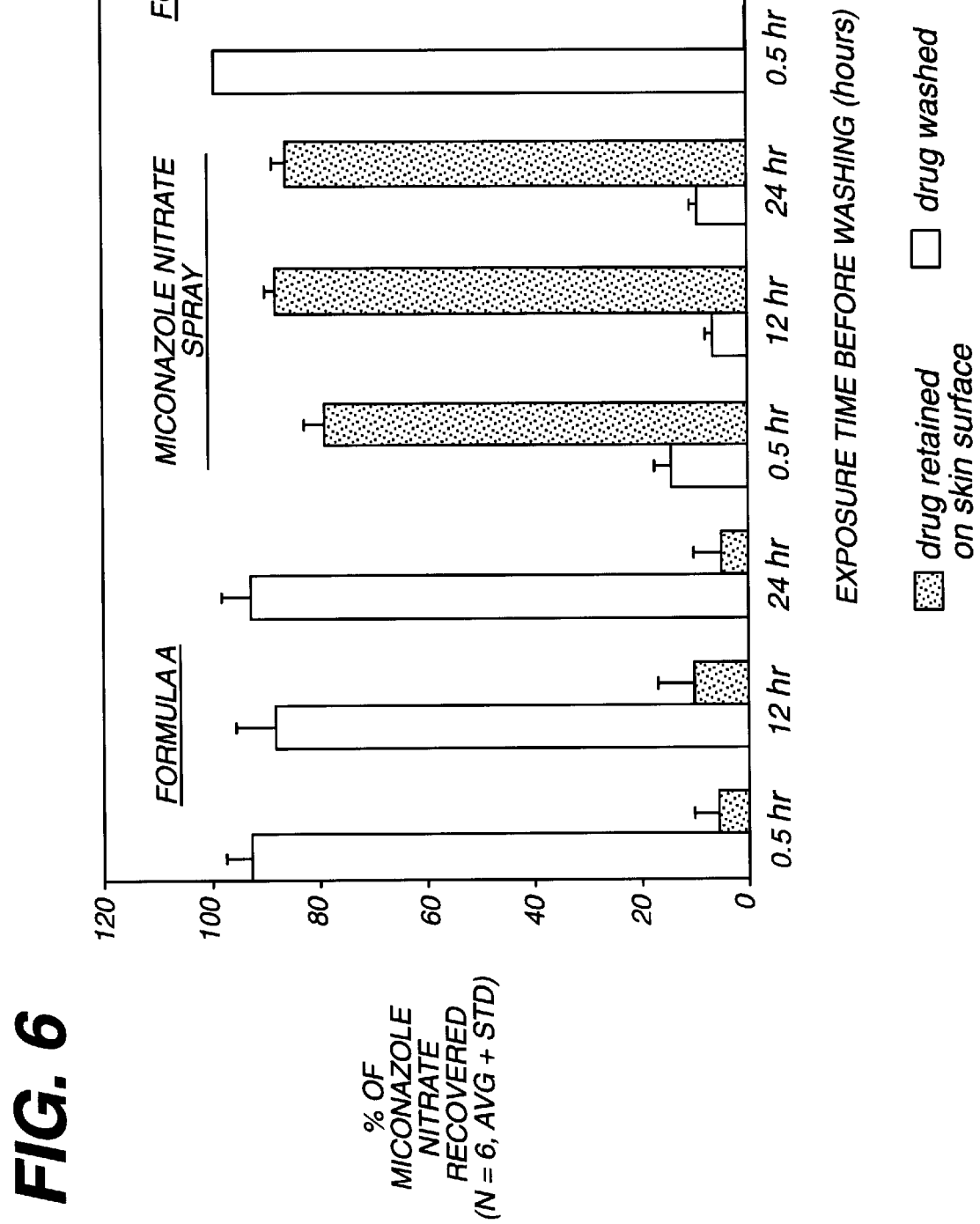
FIG. 6 is a graph which compares the amount of miconazole nitrate retained on the skin using different miconazole nitrate formulations.

As shown in FIG. 6, approximately 62–81% of miconazole nitrate was found to be retained on the skin surface after washing. In sharp contrast, the surface-retained drug for Formula A cream was less than 9%, and for Formula B aerosol was less than 0.6%. The rank order of miconazole nitrate in the Spray Formulation treated samples is the following: surface-retained (methanol swabs)>>wash liquids>epidermis>dermis>receptor fluid. On the other hand, the rank order for Formula A cream and Formula B is: wash liquids>>surface-retained>epidermis>dermis>receptor fluid. The different exposure times before washing did not have any marked effect on the substantivity results. The data confirms that the Spray Formulation indeed provides superior drug substantivity to the skin, as opposed to the commercial cream and aerosol formulations. The significantly enhanced drug retention on the skin surface by the Spray Formulation should allow a less frequent dosing regimen than the current products, and thus improve patient compliance.

Figure 7:
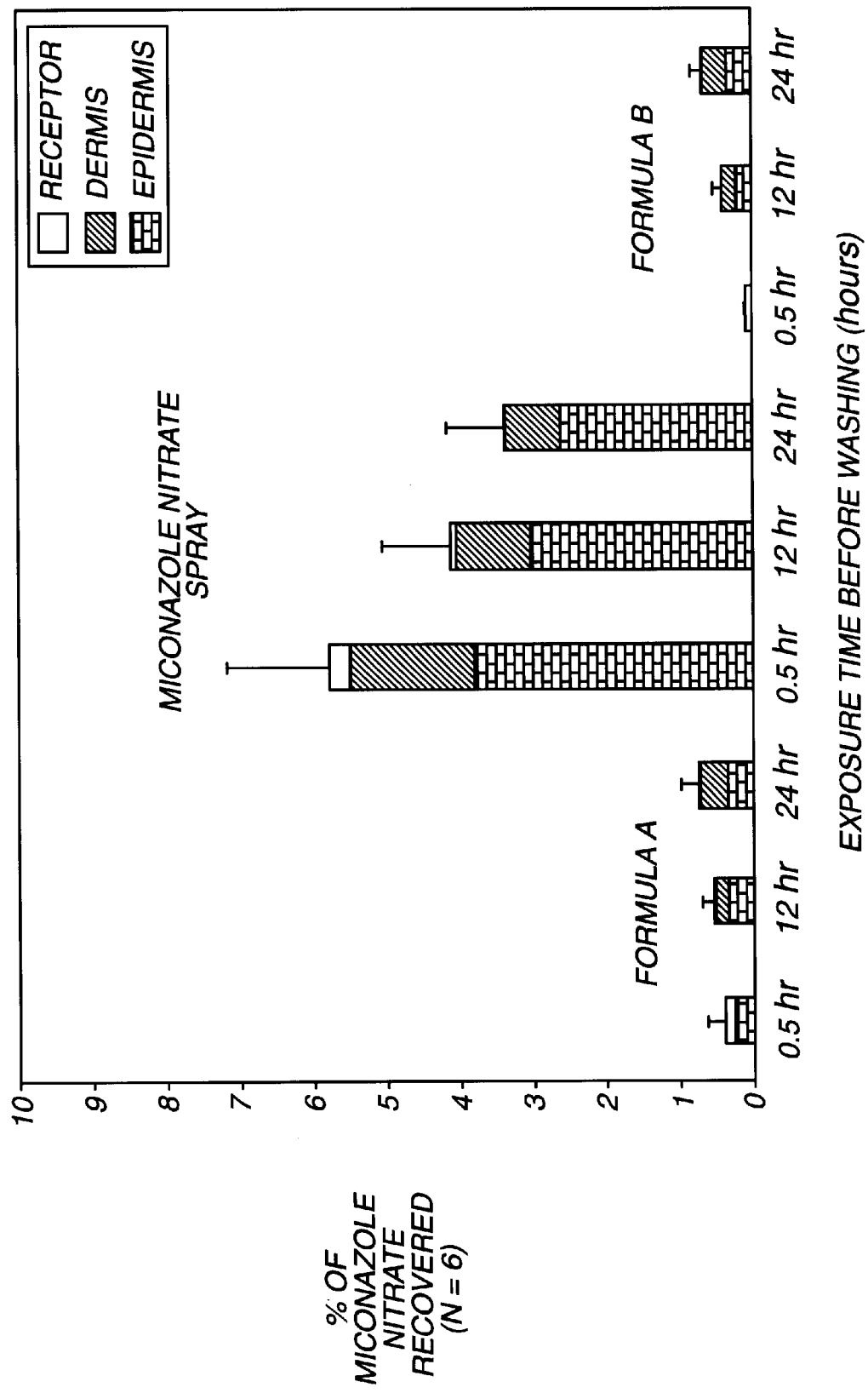
FIG. 7 shows the relative miconazole content in epidermis, dermis and receptor media.

FIG. 7 shows the relative miconazole content in epidermis, dermis and receptor media. As can be seen from the figure, miconazole concentrations in the epidermis and dermis from the Spray Formulation were several fold higher than those from the Formula A cream and Formula B aerosol. Drug content in the receptor fluid was very low. Epidermis is the target tissue for athlete's foot treatment. A higher antifungal drug concentration in epidermis would assure complete elimination of the pathogenic dermatophytes, which should enable a reduction in dosing frequency (e.g., from twice a day to once a day) and treatment duration (e.g., from four weeks to one or two weeks). There is a general trend of increasing drug penetration into the skin with prolonged skin exposure time before washing with the Formula A cream and Formula B aerosol. Interestingly, for the Spray Formulation, miconazole nitrate penetration into the skin was reduced as the exposure time before washing increased. This was probably because of the drying effect from the volatile solvents in the substantially anhydrous Spray Formulation. The drug release from the binding film might have been hindered when the skin surface was very dry. After the washing process, the residual moisture content might have facilitated the drug release and, thus increased drug penetration into the skin. Since the dermatophytes causing the athlete's foot tend to prevail in a high moisture environment, the unique moisture-triggering drug release from the Spray Formulation should be beneficial to the athlete's foot treatment.

Based on the amount of miconazole nitrate washed off or retained on the skin among the three formulations tested, it can be concluded that the newly developed miconazole nitrate Spray Formulation provides superior skin substantivity over the two commercial products tested (i.e., Formula A cream and Formula B spray liquid aerosol). The significantly enhanced drug retention on the skin surface by the Spray Formulation should allow a less frequent dosing regimen than the current products, and thus improve patient compliance. In addition, several fold more miconazole can be delivered into the skin by the Spray Formulation as opposed to the commercial products. Because epidermis is the target tissue for athlete's foot treatment, a higher antifungal drug concentration in epidermis would assure complete elimination of the pathogenic dermatophytes. These findings confirmed that the present invention resulted in a better topical antifungal product for athlete's foot treatment, which is more patient-friendly with a reduced dosing frequency and treatment duration, and likely to be more efficacious than the commercial products presently available with the same antifungal drug.

Example 10

Aerosolized Acidified Lacquer Composition

The "Spray Formulation" liquid composition in Example 9 (as shown in Table 10) was aerosolized following known procedures using dimethyl ether and a mixture of dimethyl ether with n-butane. The aerosol compositions and results are shown in Table 11. The physical appearances of the resultant aerosols were observed through transparent aerosol packages.

TABLE 11

Aerosolized miconazole nitrate lacquer and the resultant aerosols

| Composition Number | Spray Formulation (wt/wt %) | Propellant(s) (wt/wt %) | Physical appearance of resultant aerosols |
| --- | --- | --- | --- |
| 1 | 35% | 65% dimethyl ether | Clear liquid, one phase system |
| 2 | 35 | 45% dimethyl ether 20% n-butane | Clear liquid, one phase system |
| 3 | 35 | 30% dimethyl ether 35% n-butane | Turbid liquid, two phase system |

The aerosolized lacquer compositions 1 & 2 are preferable aersols with good content uniformity, where as the composition 3 is less desirable since the precipitation would likely cause non-uniform deposition of the drug during application, and would also likely to result in malfunction of the aerosol spray valve by clogging up the orifice.

Example 11

Drug Partitioning Studies With Various Concentrations of Acidifiers

Drug partitioning studies were conducted to evaluate formulation acidity on nail uptake of miconazole nitrate from nine nail lacquer formulations. All the formulations contain the same drug concentration (2% miconazole nitrate), but different amount of acidity modifiers, namely, concentrated HCl (37% HCl) 2%, 1.5%, 1%, 0.5% and 0%, or concentrated NaOH solution (10% NaOH in distilled water) 0.5%, 1%, 1.5%, and 2%. The rest of the formulations include 1% isopropyl myristate, 40% ethyl acetate, 15% Carboset® 525, and ethyl alcohol to 100%. (All the percentages cited are by weight). The experiments were conducted in triplicate, and experimental procedures were the same as those described in Example 3. The resultant nail drug contents are tabulated in the following table. The enhancement ratio refers to the ratio of a nail drug content from a lacquer containing an acidity modifier to that from a lacquer containing no acidity modifier (i.e., Formulation No. 5). It can be seen that both HCl and NaOH increased drug uptake into the nail. The extent of the increase in drug uptake is much greater with HCl. The highest drug uptake occurred with 0.5% concentrated HCl, followed by 1% concentrated HCl.

TABLE 12

| Formulation Number. | Conc. HCl (37%) Added (w/w %) | Conc. NaOH (10%) Added (w/w %) | Miconazole Nitr in nail (mg drug/gm nail) AVG | STD | Enhancement Ratio |
|---|---|---|---|---|---|
| 1 | 2 | — | 1.36 | 0.07 | 10.5 |
| 2 | 1.5 | — | 1.48 | 0.23 | 11.5 |
| 3 | 1 | — | 1.63 | 0.37 | 12.6 |
| 4 | 0.5 | — | 1.89 | 0.24 | 14.6 |
| 5 | 0 | — | 0.13 | 0.04 | 1.0 |
| 6 | — | 0.5 | 0.16 | 0.08 | 1.2 |
| 7 | — | 1 | 0.30 | 0.03 | 2.3 |
| 8 | — | 1.5 | 0.25 | 0.01 | 2.0 |
| 9 | — | 2 | 0.25 | 0.03 | 2.0 |

What is claimed is:

1. An acidified composition comprising at least one active agent, at least one acidifier, and at least one volatile solvent, wherein said at least one acidifier is HCl.

2. The composition of claim 1 wherein said at least one acidifier is 37% HCl or 10% HCl.

3. The composition of claim 1 wherein said at least one volatile solvent is selected from a member of the group consisting of ethyl alcohol, isopropyl alcohol, ethyl acetate, butyl acetate, and acetone and mixtures thereof.

4. The composition of claim 1 wherein said at least one volatile solvent is selected from the group consisting of ethyl alcohol, isopropyl alcohol, or ethyl acetate and mixtures thereof.

5. The composition of claim 1 wherein said at least one active agent is selected from the group consisting of miconazole, econazole, ketoconazole, itraconazole, fluconazole, bifoconazole, terconazole, butoconazole, tioconazole, oxiconazole, sulconazole, saperconazole, clotrimazole, butenafine, undecylenic acid, haloprogin, tolnaftate, nystatin, ciclopirox olamine, terbinafine, amorolfine, naftifine, elubiol, griseofulvin, corticosteroids, calcipotriene, anthraline, minoxidil, minoxidil sulfate, retinoids, cysteine and acetyl cysteine, methionine, glutathione, biotin, finasteride and ethocyn, tea tree oil, mupirocin, neomycin sulfate bacitracin, polymyxin B, l-ofloxacin, chlortetracycline hydrochloride, oxytetracycline hydrochloride, tetracycline hydrochoride, clindamycin phosphate, gentamicin sulfate, benzalkonium chloride, benzethonium chloride, hexylresorcinol, methylbenzethonium chloride, phenol, quaternary ammonium compounds, triclocarbon, triclosan, and pharmaceutically acceptable salts thereof.

6. An acidified lacquer composition comprising at least one active agent, at least one acidifier, at least one volatile solvent, and at least one polymeric film former, wherein said at least one acidifier is HCl.

7. The acidified lacquer composition of claim 6 wherein said at least one polymeric film former is selected from the group consisting of acrylic copolymers/acrylic polymers, polymers of methacrylic acid, esters of polymers of methacrylic acid, cellulose polymers, nitrocellulose, methyl cellulose, ethyl cellulose, cellulose acetates, cellulose triacetate, cellulose acetate butyrate, nylon, polyvinyl acetate, polyvinyl acetate phthalate, and formaldehyde resin.

8. An acidified lacquer composition comprising at least one active agent, at least one acidifier, at least one volatile solvent, and at least one polymeric film former wherein said at least one active agent is present at a concentration from about 0.1% to about 5%;

said at least one acidifier is present at a concentration from about 0.1% to about 5%;

said at least one volatile solvent is present at a concentration from about 70% to about 95%; and said at least one polymeric film former is present at a concentration from about 0.1% to about 15%, wherein said at least one polymeric film former is selected from the group consisting of acrylic copolymers/acrylic polymers, polymers of methacrylic acid, esters of polymers of methacrylic acid, cellulose polymers nitrocellulose, methyl cellulose, ethyl cellulose, cellulose acetates cellulose triacetate, cellulose acetate butyrate, nylon, polyvinyl acetate, polyvinyl acetate phthalate, and formaldehyde resin.

9. The acidified lacquer composition of claim 8 wherein said at least one active agent is selected from the group consisting of miconazole, econazole, ketoconazole, itraconazole, fluconazole, bifoconazole, terconazole, butoconazole, tioconazole, oxiconazole, sulconazole, saperconazole, clotrimazole, butenafine, undecylenic acid, haloprogin, tolnaftate, nystatin, ciclopirox olamine, terbinafine, amorolfine, naftifine, elubiol, griseofulvin, corticosteroids, calcipotriene, anthraline, minoxidil, minoxidil sulfate, retinoids, cysteine, acetyl cysteine, methionine, glutathione, biotin, finasteride and ethocyn, tea tree oil, mupirocin, neomycin sulfate bacitracin, polymyxin B, l-ofloxacin, chlortetracycline hydrochloride, oxytetracycline hydrochloride, tetrachcycline hydrochoride, clindamycin phsphate, gentamicin sulfate, benzalkonium chloride, benzethonium chloride, hexylresorcinol, methylbenzethonium chloride, phenol, quaternary ammonium compounds, triclocarbon, triclosan, and pharmaceutically acceptable salts thereof.

10. An acidified lacquer composition comprising about 1% of 37% HCl, about 2% of miconazole nitrate, about 70% ethyl alcohol, about 22% ethyl acetate, and about 3% of an acrylic polymer.

11. An acidified lacquer composition comprising about 1% of 37% HCl, about 2% of miconazole nitrate, about 40% ethyl alcohol, about 22% ethyl acetate, and about 15% of an acrylic polymer.

12. An acidified lacquer composition comprising at least one active agent, at least one acidifier, at least one volatile solvent, and at least one polymeric film former, wherein said at least one active agent is about 0.5% to about 2% of an antifungal drug, said at least one acidifier is about 0.1% to about 1% of 37% HCl, said at least one non-volatile solvent is about 40% ethyl alcohol and about 42% to about 44% ethyl acetate, and said at least one polymeric film former is about 15% of an acrylic polymer.

13. The acidified lacquer composition of claim 6 wherein said at least one active agent is about 0.5% to about 2% of an antifungal drug, said at least one acidifier is about 0.1% to about 1% of 37% HCl, said at least one non-volatile solvent is about 70% ethyl alcohol and about 23% to about 24% ethyl acetate, and said at least one polymeric film former is about 3% of an acrylic polymer.

14. A method of treating disease infected human nails or skin by topically applying 1) an acidified composition comprising at least one acidifier, at least one volatile solvent, and at least one active agent; or 2) an acidified lacquer composition comprising at least one acidifier, at least one volatile solvent, at least one active agent, and at least one polymeric film former.

15. The method of claim 14 wherein said at least one acidifier is about 1% of 37% HCl; said at least one active agent is from about 0.5% to about 3% and is selected from the group consisting of miconazole, itraconazole, econazole, ketoconzaole, clotrimazole, butenifine, terbinafine, and pharmaceutically acceptable salts thereof; said at least one volatile solvent is from about 40 to about 70% ethyl alcohol and from about 23% to about 24% ethyl acetate; and said polymeric film former is from about 3% to about 15% of an acrylic polymer.

16. The method of claim 14 wherein said at least one acidifier is about 1% of 37% HCl, at least one active agent is about from about 1% to 2% miconazole nitrate, said at least one volatile solvent is from about 40 to about 70% ethyl alcohol and from about 23% to about 24% ethyl acetate, and said at least polymeric film former is from about 3% to about 15% of an acrylic polymer.

17. The method of claim 14 wherein said at least one active agent is minoxidil and further comprising at least one active agent selected from the group consisting of miconazole, itraconazole, econazole, ketoconzaole, clotrimazole, butenfine, terbinafine, and pharmaceutically acceptable salts thereof; said at least one acidifier is 37% HCl or 10% HCl; said at least one volatile solvent is selected from the group consisting of ethyl alcohol, isopropyl alcohol, or ethyl acetate; and said at least one polymeric film former is selected from the group consisting of acrylic copolymers/acrylic polymers, polymers of methacrylic acid and the esters of polymers of methacrylic acid.

18. The method of claim 14 wherein said composition or said lacquer are applied as an aerosol.

19. A method of improving and promoting healthy human nails and skin by topically applying 1) an acidified composition comprising at least one acidifier, at least one volatile solvent, and at least one active agent; or 2) an acidified lacquer composition comprising at least one acidifier, at least one volatile solvent, at least one active agent, and at least one polymeric film former.

20. A method of improving and promoting healthy human nails by topically applying 1) an acidified composition comprising at least one acidifier, at least one volatile solvent, and at least one active agent; or 2) an acidified lacquer composition comprising at least one acidifier, at least one volatile solvent, at least one active agent, and at least one polymeric film former.

21. A method of improving and promoting healthy human skin by topically applying 1) an acidified composition comprising at least one acidifier, at least one volatile solvent, and at least one active agent; or 2) an acidified lacquer composition comprising at least one acidifier, at least one volatile solvent, at least one active agent, and at least one polymeric film former.

22. The method of claim 19 wherein said at least one active agent is minoxidil and further comprising at least one active agent selected from the group consisting of miconazole, itraconazole, econazole, ketoconzaole, clotrimazole, butenafine terbinafine and pharmaceutically acceptable salts thereof; said at least one acidifier is 37% HCl or 10% HCl; said at least one volatile solvent is selected from the group consisting of ethyl alcohol, isopropyl alcohol, or ethyl acetate; and said at least one polymeric film former is selected form the group consisting of acrylic copolymers/acrylic polymers, polymers of methacrylic acid and the esters of polymers of methacrylic acid.

23. The method of claim 19 wherein said at least one active agent is selected from the group consisting of miconazole, itraconazole, econazole, ketoconzaole, clotrimazole, butenafine, terbinafine and pharmaceutically acceptable salts thereof; said at least one acidifier is 37% HCl or 10% HCl; said at least one volatile solvent is selected from the group consisting of ethyl alcohol, isopropyl alcohol, or ethyl acetate; and said at least one polymeric film former is selected form the group consisting of acrylic copolymers/acrylic polymers, polymers of methacrylic acid and the esters of polymers of methacrylic acid.

24. The method of claim 19 wherein said composition or said lacquer are applied as an aerosol.

25. The composition of claim 1, wherein said at least one active agent is an antifungal drug.

26. The composition of claim 1, wherein said at least one active agent is miconazole or a pharmaceutically acceptable salt thereof.

27. The composition of claim 4, wherein said at least one active agent is present at a concentration from about 0.1% to about 5%; said at least one acidifier is present at a concentration from about 0.1% to about 5%; and said at least one volatile solvent is present at a concentration from about 70% to about 95%.

28. The composition of claim 27 wherein said at least one active agent is selected from the group consisting of miconazole, econazole, ketoconazole, itraconazole, fluconazole, bifoconazole, terconazole, butoconazole, tioconazole, oxiconazole, sulconazole, saperconazole, clotrimazole, butenafine, undecylenic acid, haloprogin, tolnaftate, nystatin, ciclopirox olamine, terbinafine, amorolfine, naftifine, elubiol, griseofulvin, corticosteroids, calcipotriene, anthraline, minoxidil, minoxidil sulfate, retinoids, cysteine and acetyl cysteine, methionine, glutathione, biotin, finasteride and ethocyn, tea tree oil, mupirocin, neomycin sulfate bacitracin, polymyxin B, l-ofloxacin, chlortetracycline hydrochloride, oxytetracycline hydrochloride, tetrachcycline hydrochloride, clindamycin phosphate, gentamicin sulfate, benzalkonium chloride, benzethonium chloride, hexylresorcinol, methylbenzethonium chloride, phenol, quaternary ammonium compounds, triclocarbon, triclosan, and pharmaceutically acceptable salts thereof.

29. The composition of claim 27 wherein said at least one active agent is an antifungal drug.

30. The composition of claim 27, wherein said at least one active agent is miconazole or a pharmaceutically acceptable salt thereof.

31. The acidified lacquer of claim 6 wherein said at least one active agent is selected from the group consisting of miconazole, econazole, ketoconazole, itraconazole, fluconazole, bifoconazole, terconazole, butoconazole, tioconazole, oxiconazole, sulconazole, saperconazole, clotrimazole, butenafine, undecylenic acid, haloprogin, tolnaftate, nystatin, ciclopirox olamine, terbinafine, amorolfine, naftifine, elubiol, griseofulvin, corticosteroids, calcipotriene, anthraline, minoxidil, minoxidil sulfate, retinoids, cysteine and acetyl cysteine, methionine, glutathione, biotin, finasteride and ethocyn, tea tree oil, mupirocin, neomycin sulfate bacitracin, polymyxin B, l-ofloxacin, chlortetracycline hydrochloride, oxytetracycline hydrochloride, tetrachcycline hydrochloride, clindamycin phosphate, gentamicin sulfate, benzalkonium chloride, benzethonium chloride, hexylresorcinol, methylbenzethonium chloride, phenol, quaternary ammonium compounds, triclocarbon, triclosan, and pharmaceutically acceptable salts thereof.

32. The acidified lacquer of claim 6 wherein said at least one active agent is an antifungal drug.

33. The acidified lacquer of claim 6, wherein said at least one active agent is miconazole or a pharmaceutically acceptable salt thereof.

34. The acidified lacquer of claim 6 wherein said at least one volatile solvent is selected from a member of the group consisting of ethyl alcohol, isopropyl alcohol, ethyl acetate, butyl acetate, and acetone, and mixtures thereof.

35. The acidified lacquer of claim 6 wherein said at least one volatile solvent is selected from the group consisting of ethyl alcohol, isopropyl alcohol, or ethyl acetate, and mixtures thereof.

36. The acidified lacquer of claim 35 wherein said at least one polymeric film former is selected from the group consisting of acrylic copolymers/acrylic polymers, polymers of methacrylic acid, esters of polymers of methacrylic acid, cellulose polymers, nitrocellulose, methyl cellulose, ethyl cellulose, cellulose acetates cellulose triacetate, cellulose acetate butyrate, nylon, polyvinyl acetate, polyvinyl acetate phthalate, and formaldehyde resin.

37. The acidified lacquer of claim 36, wherein said at least one active agent is present at a concentration from about 0.1% to about 5%; said at least one acidifier is present at a concentration from about 0.1% to about 5%; said at least one volatile solvent is present at a concentration from about 70% to about 95%; and said at least one polymeric film former is present at a concentration from about 0.1% to about 15%.

38. The acidified lacquer of claim 37 wherein said at least one active agent is selected from the group consisting of miconazole, econazole, ketoconazole, itraconazole, fluconazole, bifoconazole, terconazole, butoconazole, tioconazole, oxiconazole, sulconazole, saperconazole, clotrimazole, butenafine, undecylenic acid, haloprogin, tolnaftate, nystatin, ciclopirox olamine, terbinafine, amorolfine, naftifine, elubiol, griseofulvin, corticosteroids, calcipotriene, anthraline, minoxidil, minoxidil sulfate, retinoids, cysteine and acetyl cysteine, methionine, glutathione, biotin, finasteride and ethocyn, tea tree oil, mupirocin, neomycin sulfate bacitracin, polymyxin B, l-ofloxacin, chlortetracycline hydrochloride, oxytetracycline hydrochloride, tetrachcycline hydrochloride, clindamycin phosphate, gentamicin sulfate, benzalkonium chloride, benzethonium chloride, hexylresorcinol, methylbenzethonium chloride, phenol, quaternary ammonium compounds, triclocarbon, triclosan, and pharmaceutically acceptable salts thereof.

39. The acidified lacquer of claim 37 wherein said at least one active agent is an antifungal drug.

40. The acidified lacquer of claim 37 wherein said at least one active agent is selected from the group consisting of miconazole or pharmaceutically acceptable salts thereof.

41. The acidified lacquer of claim 8 wherein said at least one active agent is an antifungal drug.

42. The acidified lacquer of claim 8, wherein said at least one active agent is miconazole or a pharmaceutically acceptable salt thereof.

43. The acidified lacquer of claim 8 wherein said at least one volatile solvent is selected from a member of the group consisting of ethyl alcohol, isopropyl alcohol, ethyl acetate, butyl acetate, and acetone, and mixtures thereof.

44. The acidified lacquer of claim 8 wherein said at least one volatile solvent is selected from the group consisting of ethyl alcohol, isopropyl alcohol, or ethyl acetate, and mixtures thereof.

45. The acidified lacquer of claim 8, wherein said at least one active agent is present at a concentration from about 0.1% to about 5%; said at least one acidifier is present at a concentration from about 0.1% to about 5%; said at least one volatile solvent is present at a concentration from about 70% to about 95%; and said at least one polymeric film former is present at a concentration from about 0.1% to about 15%.

46. The acidified lacquer of claim 45, wherein said at least one active agent is selected from the group consisting of miconazole, econazole, ketoconazole, itraconazole, fluconazole, bifoconazole, terconazole, butoconazole, tioconazole, oxiconazole, sulconazole, saperconazole, clotrimazole, butenafine, undecylenic acid, haloprogin, tolnaftate, nystatin, ciclopirox olamine, terbinafine, amorolfine, naftifine, elubiol, griseofulvin, corticosteroids, calcipotriene, anthraline, minoxidil, minoxidil sulfate, retinoids, cysteine and acetyl cysteine, methionine, glutathione, biotin, finasteride and ethocyn, tea tree oil, mupirocin, neomycin sulfate bacitracin, polymyxin B, l-ofloxacin, chlortetracycline hydrochloride, oxytetracycline hydrochloride, tetrachcycline hydrochloride, clindamycin phosphate, gentamicin sulfate, benzalkonium chloride, benzethonium chloride, hexylresorcinol, methylbenzethonium chloride, phenol, quaternary ammonium compounds, triclocarbon, triclosan, and pharmaceutically acceptable salts thereof.

47. The acidified lacquer of claim 45 wherein said at least one active agent is an antifungal drug.

48. The acidified lacquer of claim 45 wherein said at least one active agent is selected from the group consisting of miconazole or pharmaceutically acceptable salts thereof.

* * * * *